(12) United States Patent
Farhadi

(10) Patent No.: US 9,993,137 B2
(45) Date of Patent: Jun. 12, 2018

(54) ENDOSCOPE ACCESSORY

(71) Applicant: Ashkan Farhadi, Irvine, CA (US)

(72) Inventor: Ashkan Farhadi, Irvine, CA (US)

( * ) Notice: Subject to any disclaimer, the term of this patent is extended or adjusted under 35 U.S.C. 154(b) by 216 days.

(21) Appl. No.: 14/121,563

(22) Filed: Sep. 18, 2014

(65) Prior Publication Data

US 2016/0081536 A1    Mar. 24, 2016

(51) Int. Cl.
| | | |
|---|---|---|
| *A61B 1/00* | (2006.01) | |
| *A61B 1/273* | (2006.01) | |
| *A61B 8/12* | (2006.01) | |
| *A61B 1/015* | (2006.01) | |
| *A61B 1/012* | (2006.01) | |
| *A61B 1/018* | (2006.01) | |
| *A61B 8/00* | (2006.01) | |
| *A61M 25/06* | (2006.01) | |
| *A61B 1/005* | (2006.01) | |
| *A61M 25/10* | (2013.01) | |

(52) U.S. Cl.
CPC ...... *A61B 1/00135* (2013.01); *A61B 1/00082* (2013.01); *A61B 1/00094* (2013.01); *A61B 1/00137* (2013.01); *A61B 1/00147* (2013.01); *A61B 1/00154* (2013.01); *A61B 1/015* (2013.01); *A61B 1/018* (2013.01); *A61B 1/0125* (2013.01); *A61B 1/2736* (2013.01); *A61B 8/12* (2013.01); *A61B 8/445* (2013.01); *A61M 25/0662* (2013.01); *A61B 1/005* (2013.01); *A61M 25/1011* (2013.01); *A61M 2025/1052* (2013.01)

(58) Field of Classification Search
USPC .................................. 600/115–116, 121–125
See application file for complete search history.

(56) References Cited

U.S. PATENT DOCUMENTS

| | | | | |
|---|---|---|---|---|
| 4,453,545 A | * | 6/1984 | Inoue | A61M 16/04 128/207.15 |
| 5,217,001 A | * | 6/1993 | Nakao | A61B 1/00135 24/DIG. 50 |
| 6,234,958 B1 | * | 5/2001 | Snoke | A61B 1/00082 600/106 |

(Continued)

*Primary Examiner* — Alexandra L Newton

(57) ABSTRACT

This invention relates generally to a diagnostic and therapeutic device. According to some aspects of the invention, the device may be composed of a flexible sheet that is wrapped around the endoscope shaft to form a flexible overtube. The overtube may include an inflatable positioning ring that may be inflated after placement of the overtube just proximal to the tip of the endoscope or colonoscope to secure the position of the overtube within the body cavity. The overtube also may include an inflatable sealing band within the internal surface of the overtube that when inflated create a seal around the endoscope shaft. According to other aspects of the invention, the device may be a catheter with an occlusion balloon at its free end portion that is carried by the overtube and extends beyond the tip of the endoscope. Inflation of the positioning ring, sealing band and occlusion balloon may define an examination compartment within the body cavity at the tip of the endoscope. The examination compartment may be filled with air, or with water, depending on applications. In addition the examination compartment can be thoroughly lavaged using the irrigation tube system.

10 Claims, 34 Drawing Sheets

(56) References Cited

U.S. PATENT DOCUMENTS

| | | | |
|---|---|---|---|
| 8,225,794 B2* | 7/2012 | Mikkaichi | A61B 1/273 128/200.26 |
| 2006/0161044 A1* | 7/2006 | Oneda | A61B 1/00082 600/116 |
| 2009/0227835 A1* | 9/2009 | Terliuc | A61B 1/00082 600/106 |
| 2011/0251458 A1* | 10/2011 | Terliuc | A61B 1/00082 600/116 |

* cited by examiner

ENDOSCOPE ACCESSORY

CROSS-REFERENCE TO RELATED APPLICATIONS

This application is a continuation-in-part of U.S. Ser. No. 13/900,524 filed on May 22, 2013 which is a continuation-in-part of U.S. Ser. No. 12/266,953 filed on Nov. 7, 2008, both of which are incorporated herein by reference.

I. FIELD OF INVENTION

Some embodiments of the present invention relates generally to the field of endoscopy and, more particularly, to an endoscope accessory for improving endoscopic examination of body organs, particularly the gastrointestinal tract.

II. BACKGROUND OF INVENTION

Endoscopy is a well-known procedure for examining the internal organs. The procedure is performed under the guidance of an endoscope. Currently used fiber optic endoscopes include lenses mounted in a flexible tube that relay an image from inside a body cavity for viewing by a physician for diagnosis or manipulation inside the body cavity.

In performing an endoscopy, it is common to insufflate (introduce air into) the gastrointestinal tract in order to provide easier visualization. This can cause bloating and discomfort to the patient or, in rare cases, severe abdominal pain.

More recently, echoendoscopy has been introduced. An echoendoscope (EUS) is a device that combines endoscopy and ultrasound to image the gastrointestinal wall and surrounding structures.

The ultrasound transducer is positioned at the distal tip of endoscope; the key components of the transducer are the piezoelectric crystals that vibrate to produce ultrasonic waves. The ultrasonic waves travel through the gastrointestinal wall and beyond the visceral wall into the surrounding organs. The reflection of these ultrasound waves is detected by the same crystals at the transducer and reconstruction of these reflections will result in creating a real time image of the gastrointestinal wall and its surrounding structures. The ultrasonic wave reflects from the surface of structures with different density and can pass very well through fluid containing and solid structures. Air, however, creates a barrier to ultrasonic wave passage and hampers the obtaining of ultrasonic images.

Several attempts have been made to minimize the amount of interfering air between the transducer and the examining structure. The prior art teaches the use of balloons at the end of the endoscope that encloses the transducer and is filled with water to permit acoustic coupling between the transducer and the luminal wall or other gastrointestinal structures. This is particularly helpful in the part of the gastrointestinal tract where the diameter of the lumen is small and the inflated balloon makes good circumferential contact with the intestinal wall and thus creates a good acoustic coupling. In most parts of the gastrointestinal tract, however, the large diameter of the lumen and/or the angle of the transducer in relation to the intestinal wall results in an inadequate contact between the transducer balloon and the intestinal wall. Therefore, operators usually use water infusion to fill the region of the gastrointestinal tract with water and create acoustic coupling between the transducer and the examined structures.

A significant shortcoming of this prior art is that it does not account for the fact that the gastrointestinal tract is not a closed region and the infused water soon moves to other regions of the gastrointestinal tract. Infusion of significant amounts of water during the examination could result in untoward problems such as aspiration of the water into the patient's airway or overdistention of the gastrointestinal tract.

Further advances in the prior art include two-balloon approaches for assisting the movement of the endoscope. However, these prior art devices utilize the balloons only to secure and maintain positioning of the endoscope or to seal two separate anatomical structures from one another. Yet further attempts have taught the use of an overtube that consists of a device having a window near its distal end through which the endoscopic examination can be performed. A shortcoming of this approach is that it limits the maneuverability of the endoscope and may create noise, thereby diminishing the accuracy of a procedure.

There is need, therefore, for an examination accessory for endoscopic examination that creates an examination partition around the endoscope tip. Such a device will create an examination compartment proximal and distal to the endoscope or ultrasound tip. The examination compartment can then be filled with air, water or could be thoroughly lavaged using the device. Such a device may further include balloons comprising at least a positioning ring for maintaining the position of the endoscope tip in an area to be examined and to seal the proximal end of the examination partition and may include an independently positionable occlusion balloon distal to the tip of the endoscope or echoendoscope for sealing the distal end of the examination partition. There is further need for such a device that can be placed on an endoscope shaft without the necessity of having to remove the endoscope from the body. Some embodiments of the present invention provides such a device.

III. SUMMARY OF THE INVENTION

Some embodiments of the present invention improves endoscopic examination by enhancing and maintaining luminal view by deploying the proposed device, the device may include at least one flexible elongated sheet, sized to envelop a flexible endoscope or echoendoscope shaft and may envelop an endoscope or echoendoscope shaft without need to remove endoscope from the body; its opposed longitudinal edge portions may coact to form a flexible overtube receiving therewithin the endoscope or echoendoscope shaft.

The longitudinal edges of the endoscope accessory may be supplied with an adhesive along its entire length for coacting with the opposed edge portions to form a liquid tight seam along the entire length of the overtube. The adhesive may be covered by a release sheet that can be removed before adhering the two longitudinal end portions.

Alternative embodiments to using adhesive at the longitudinal edges of the endoscope accessory for creating the longitudinal seam may include using a plurality of spaced magnets on the longitudinal edge portions of the endoscope accessory sheet that are attracting the other magnets interspersed on the other longitudinal edge portion. To avoid activation of the magnets before placing the endoscope shaft within the overtube, at least one longitudinal edge portion may be supplied with a longitudinal magnet cover. Both longitudinal edge portions may be provided with a cover. The magnets can only coact with the opposed longitudinal edge portion magnets when the magnet covers are removed from the edge portion or portions.

The overtube may be provided with a handle on the external surface at the proximal end of the overtube for grasping and manipulation of the overtube within the body cavity. The handle is also the hub where a plurality of external inflation tubes and an irrigation port may connect to the overtube and may be used for connection of the overtube to inflation device, suction device, irrigation tube system or passage of therapeutic tools through the overtube.

The overtube may further include at least one inflatable positioning ring on external surface of the distal end portion of the flexible overtube for securing the position of the overtube within the body cavity. The inflated positioning ring may be asymmetric or eccentric in regard to the overtube. This allows a better sealing created by inflatable positioning ring within the body cavity and also improves the maneuverability of the endoscope tip within the body cavity.

The overtube may further include at least one positioning ring inflation tube in communication with the inflatable positioning ring for inflating or deflating the inflatable positioning ring.

The overtube may further include at least one inflatable sealing band on the internal surface of the overtube at the proximal end portion of the overtube, proximal to the irrigation port for creation a seal around the endoscope shaft within the overtube. Alternatively, the inflatable sealing band may be replaced with an elastomeric sealing bead on the internal surface of the flexible overtube. The inflated sealing band may be eccentric to the overtube. This allows a better seal created by inflatable sealing band over endoscope. Alternatively, the sealing band may be positioned on the internal surface of the overtube at the mid portion, or distal end portion of the overtube. Alternatively there could be more than one sealing band within the internal surface of the overtube.

The overtube may further include at least one sealing band inflation tube for inflating or deflating the inflatable sealing band.

The overtube may further include at least one catheter passageway which defines a passageway for passing catheter or other accessories such as biopsy forceps and other endoscopic accessories from the overtube proximal end portion to the overtube distal end portion.

The endoscope accessory may also include at least one occlusion catheter carried by the overtube through the catheter passageway, having a free, independently positionable distal end portion that terminates in an inflatable occlusion balloon. The occlusion catheter may include at least one occlusion balloon tube for inflating or deflating of the inflatable occlusion balloon and at least one a suction tube that terminates in a suction tip downstream of the occlusion balloon that facilitates removal of secretions of body cavity distal to the occlusion balloon.

The endoscope accessory may also include at least one irrigation port. The irrigation port may be situated on the overtube handle and may include a closeable lid.

The irrigation port may allow a direct access to the lumen of the overtube. The irrigation port may be connected to irrigation tubes that can deliver water into or drain water out of the examination compartment in the gastrointestinal tract through the lumen of the overtube.

The overtube may further include at least one fluid conduit that defines a passageway for inflating or suctioning fluid or air within the examination compartment within the body cavity at the distal end of the overtube.

The overtube may further include at least a suction conduit connected to a suction port situated on the external surface of the overtube between the inflatable positioning ring and the proximal end portion of the overtube. The suction port may be used to remove the secretions that accumulate proximal to the inflatable positioning ring in the body cavity.

Alternatively, the longitudinal edge portions can be supplied with plurality of spaced magnets covered by a magnet cover comprised of a slit sleeve and the like. The magnets on the longitudinal edge portions are able to coact upon removal of the magnet cover. The magnet pieces on one edge portion are interspersed with the spaced magnets on the other longitudinal edge portion to form the seam. Alternatively, the seam may be created by self-fusing silicon tape, other interlocking mechanisms such as tongue and groove, hook and loop, zip-lock-type fastener and the like or a combination of these mechanisms.

In use, the endoscope accessory of the claimed invention is a flexible, elongated sheet that envelops an endoscope or echoendoscope shaft while the endoscope shaft is still within the body cavity without the need to remove the endoscope or pre-position the overtube over the endoscope shaft prior to the endoscope insertion within the body cavity. However, as those skilled in the arts will understand, the device could be placed prior to endoscope insertion.

After enveloping or surrounding the endoscope shaft by the sheet, the opposing longitudinal edge portions may be joined to form an overtube by creating a longitudinal seam along the entire length of the overtube. The opposed longitudinal edge portions of the sheet may be supplied with adhesive, covered by a release sheet. To form the overtube, the release sheet is removed and the opposed longitudinal edge portions coact using adhesive to form a liquid tight seam.

After closure of the overtube seam along the overtube's length, the endoscope shaft is enveloped within the overtube, the handle of the overtube is grasped and the overtube is pushed into the body cavity of a patient with the guide of the endoscope shaft to be placed at the desired location, just proximal to the tip of the endoscope. The inflatable positioning ring is inflated to secure the position of the overtube distal end portion within the body cavity.

The inflatable sealing band may be inflated to secure the position of the endoscope within the overtube and create a seal around the endoscope shaft at the proximal end portion of the overtube. The endoscope may be replaced when the inflatable sealing band is not inflated, if desired, with another endoscope while the overtube stays in its position within the body cavity.

The occlusion balloon catheter is passed through the catheter passageway to be placed beyond the distal tip of the overtube. After the inflatable occlusion balloon exits the catheter passageway at the distal tip of the overtube, it is placed at the desired location, distal to the distal tip of the endoscope. Then, the inflatable occlusion balloon is inflated.

Inflation of the occlusion balloon creates an examination compartment which is defined by the inflated positioning ring, inflated sealing band and the inflated occlusion balloon around the tip for the endoscope at the distal end of the overtube.

The examination compartment can be filled with air, or water, depending on applications. In addition the examination compartment may be thoroughly lavaged using the irrigation tubes connected to irrigation port or the proximal overtube opening. During the irrigation process the inflated balloons prevent escape of air or water from the examination compartment. During the irrigation process, the endoscope tip can remain at the examination compartment, be pulled back to the proximal end portion of the overtube or be completely removed. In the latter case the proximal opening of the overtube can be closed shut using a proximal overtube opening cap.

Throughout the procedure, pressure within the examination compartment may be maintained and monitored using the fluid conduits.

After termination of the examination, the positioning ring, sealing band and occlusion balloon are all deflated and the overtube is removed independent of, or together with, the endoscope.

IV. BRIEF DESCRIPTION OF THE DRAWINGS

V. DETAILED DESCRIPTION OF THE INVENTION

Figure 1:
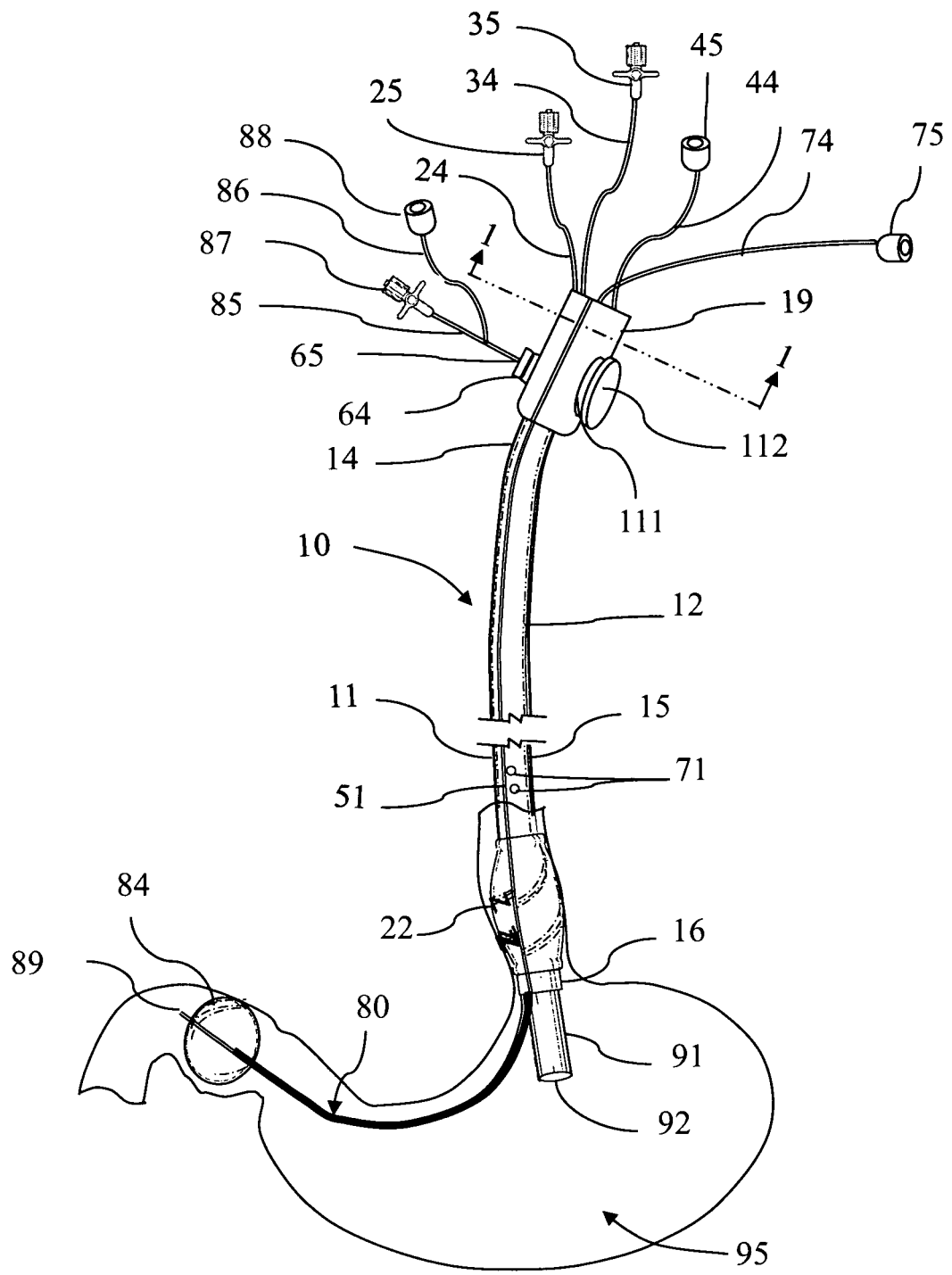
FIG. 1 is a schematic illustration of the device within the upper gastrointestinal tract.

Before explaining some aspects of embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Unless defined otherwise, all technical and scientific terms used herein have the same meaning as commonly understood by one of ordinary skill in the art to which this invention belongs. Moreover, the singular forms "a", "an", and "the" include plural referents unless the context clearly dictates otherwise.

Use of the word endoscope includes any device that would benefit from the use of an endoscopy accessory made according to the principles of the invention for examination, diagnosis or treatment.

Use of the word endoscope or echoendoscope is meant to include both unless context dictates otherwise.

Use of the word water is also meant to include any useful fluid, including but not limited to medicants or gels.

Additionally, while the word examination is used, it is meant to include also diagnosis, treatment or therapy as may be the case.

According to certain embodiments of the present invention, an endoscope accessory 10 may include:

A—Overtube: As it is depicted in FIG. 1, an overtube 11, as shown in FIG. 1, which may defines an essentially cylindrical central through passageway for receiving therewithin an endoscope or echoendoscope shaft 91 and then is inserted inside a body cavity such as gastrointestinal tract.

Overtube 11 has an external surface 12 and an internal surface (not shown in FIG. 1), a proximal end portion 14, a midportion 15, a distal end portion 16, a proximal opening 17 and a distal opening 18. Overtube 11 may include at least one handle 19 at its proximal end portion 14. Handle 19 on the external surface 12 at the proximal end portion 14 of the overtube 11 is for grasping and manipulation of the overtube 11 within the body cavity. Handle 19 is also a hub where a plurality of external inflation tubes and irrigation port may connect to overtube 11 and may be used for connection of the overtube to inflation device, suction device, irrigation tubes or passage of therapeutic tools through overtube 11.

The length of overtube 11 may be long enough so that when the distal end portion 16 of the overtube 11 is secured inside the body cavity, the overtube proximal end portion 14 stays out of the body cavity and allows grasping of the handle 19 and manipulation of overtube 11 for proper positioning of the overtube distal end portion 16 within the body cavity by the operator. The diameter of overtube 11 may be wide enough to freely receive a regular endoscope or echoendoscope shaft 91 therewithin. Within the body cavity, the endoscope tip 92 extends beyond overtube 11 distal end portion 16, as shown in FIG. 1, for detailed examination of the body cavity. Overtube 11 may include a longitudinal seam 51 along its entire length that allows opening of overtube 11 along its entire length for placing the endoscope shaft 91 within overtube 11 without the need for removing endoscope shaft 91 from the body cavity.

Figure 2:
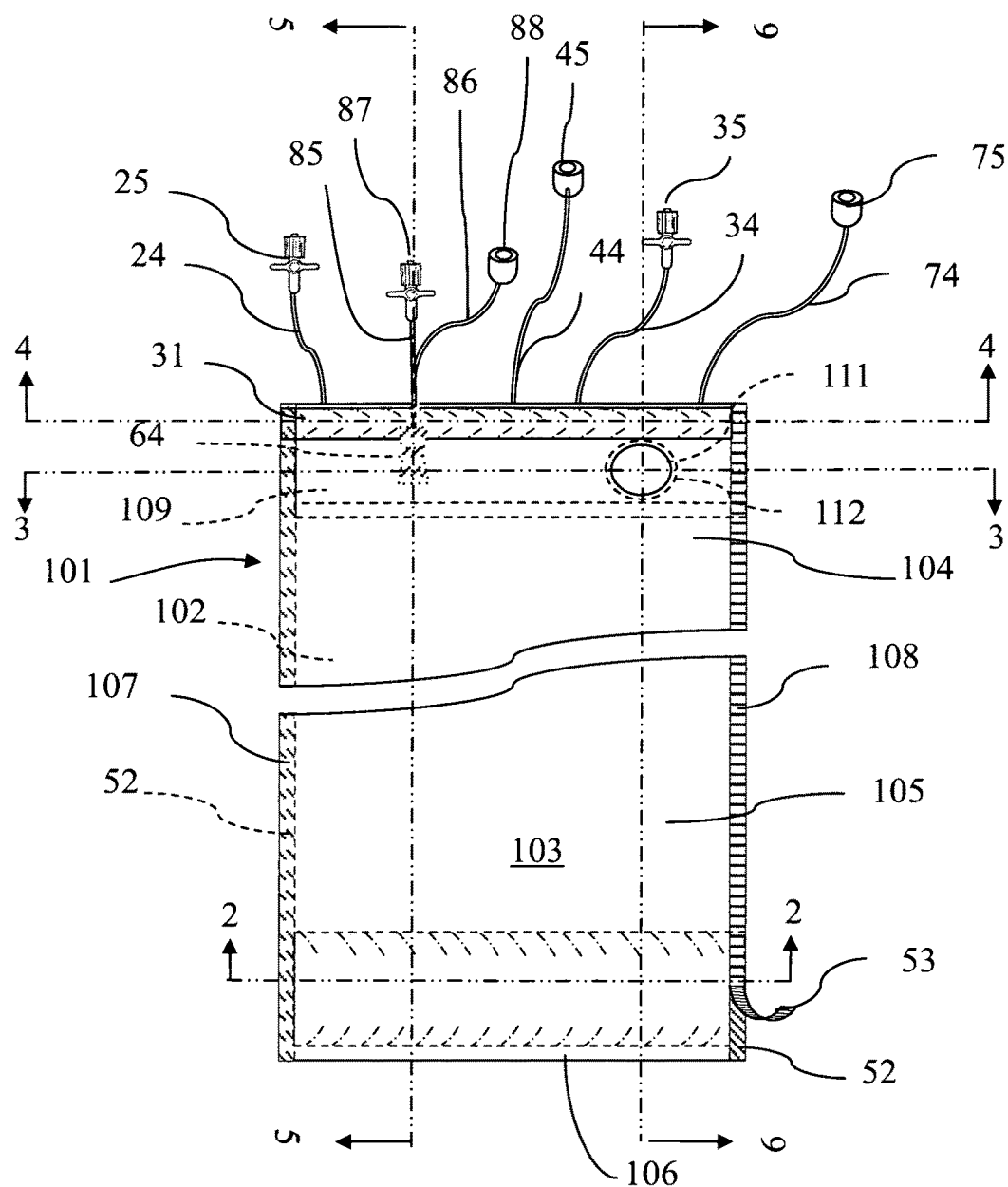
FIG. 2 is a plan view of the present invention.

As it is depicted in FIG. 2, overtube 11 of the endoscope accessory 10 may include a flexible elongated sheet 101, sized to removably envelop the flexible endoscope or echoendoscope shaft 91, having face 102 and face 103, a proximal end portion 104, a midportion 105, a distal end portion 106, and opposed longitudinal edge portions 107 and 108 that may coact reversibly to form a flexible overtube 11 (FIG. 1). Overtube 11 can be made of any suitable material. The irrigation port 111 projects over the strip 109 and is capped by the irrigation port cap 112. Face 103 forms inner surface 13 (shown in FIG. 8) of overtube 11 which defines a central through passageway for receiving therewithin the endoscope or echoendoscope shaft 91 which may be inserted inside a body cavity such as gastrointestinal tract (FIG. 1).

The sheet 101, which forms overtube 11, is further provided with a strip 109 on face 102 of the sheet 101, which may extend across the entire width of the sheet 101 at the proximal end portion 104 of the sheet 101. In overtube 11, strip 109 forms handle 19 on the external surface 12 of flexible overtube 11 when the opposed longitudinal edge portions 107 and 108 coact to form overtube 11 (FIG. 1).

The opposed longitudinal edge portions 107 and 108 may be supplied with an adhesive 52 covered by a release sheet 53. After removal of release sheet 53 from adhesive 52 at opposed longitudinal edge portions 107 and 108, opposed longitudinal edge portions 107 and 108 may be overlapped to form longitudinal seam 51 along the entire length of overtube 11 (FIG. 1) to form an essentially cylindrical and hollow member.

Figure 3:
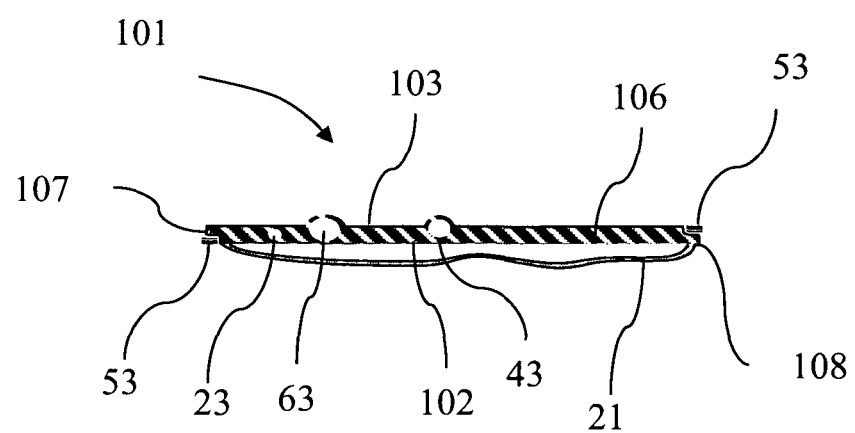
FIG. 3 is a sectional view of the device shown in FIG. 2 taken along plane 2-2.

As it is depicted in FIG. 3, sheet 101 may further include a catheter passageway 63 and a fluid conduit 43.

An inflatable pocket 21 on face 102 of sheet 101, extends across the entire width of sheet 101 at the distal end portion 106 of the sheet 101, forming an inflatable positioning ring 22 (FIG. 1) on external surface 12 of overtube 11.

Figure 4:
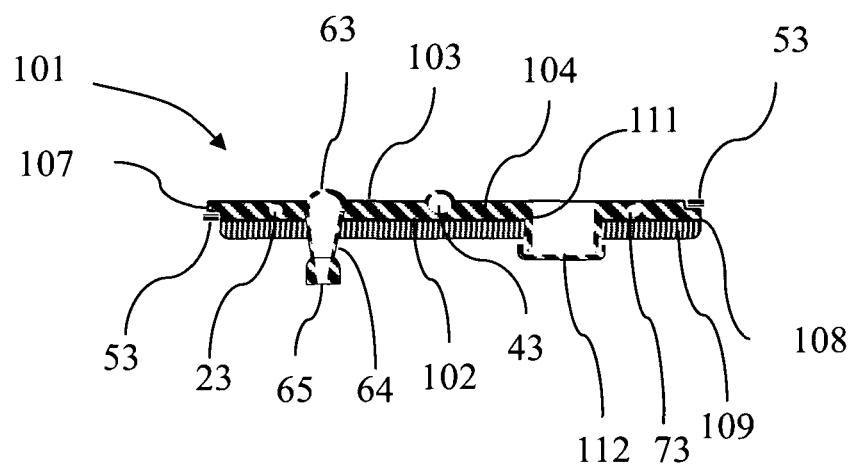
FIG. 4 is a sectional view of the device shown in FIG. 2 taken along plane 3-3.
Figure 6:
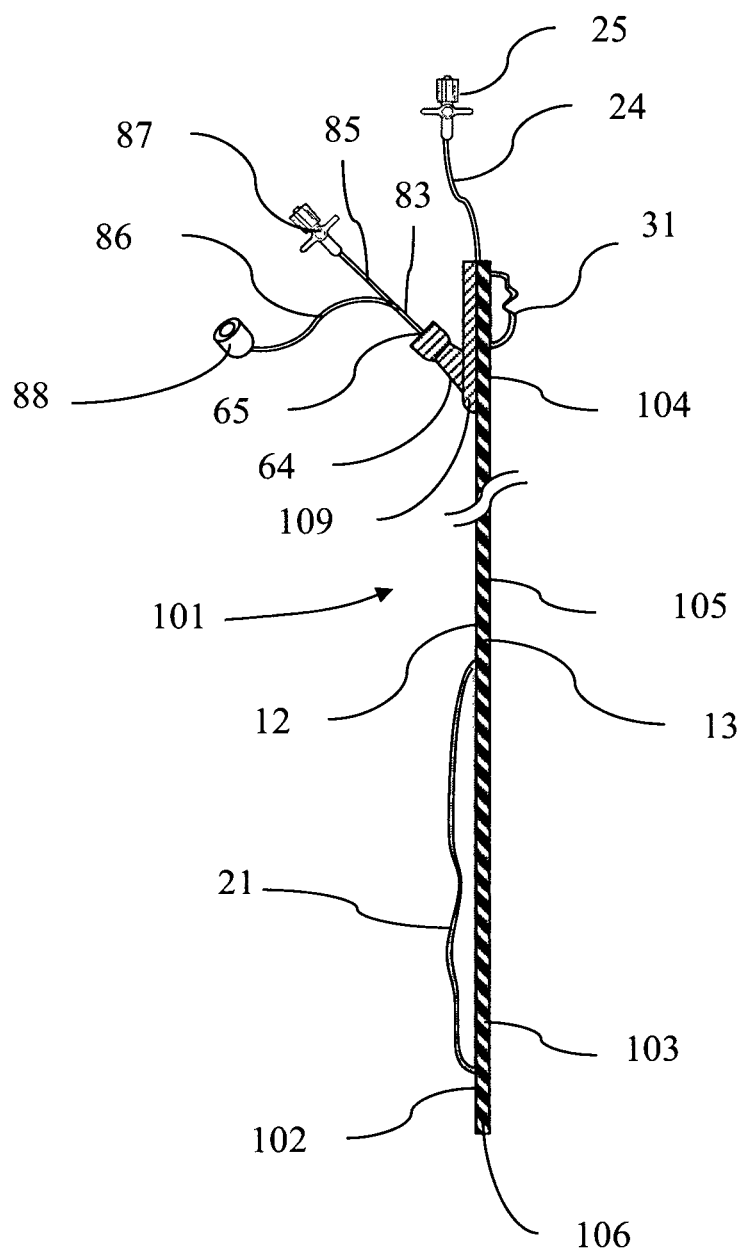
FIG. 6 is a longitudinal sectional view of the device shown in FIG. 2 taken along plane 5-5.

As it is depicted in FIG. 4, the catheter passageway 63 may extend outward as a catheter port projection 64 over the strip 109 at the proximal end portion 104 of sheet 101 (Also in FIG. 6). Catheter passageway 63 terminates in a catheter entrance port 65 at the tip of catheter port projection 64. Catheter passageway 63 defines a through passageway for receiving therewithin a catheter or other endoscopic accessories. After opposed longitudinal edge portions 107 and 108 coact to form flexible overtube 11, catheter passageway 63 may be used for passing a catheter or an endoscope accessory device by overtube 11. A catheter or endoscopic accessory device may be inserted into catheter entrance port 65 on catheter port projection 64 and passed through catheter passageway 63 and exit from the catheter exit port 61 (shown in FIG. 11) inside the body cavity, such as the gastrointestinal tract.

Figure 5:
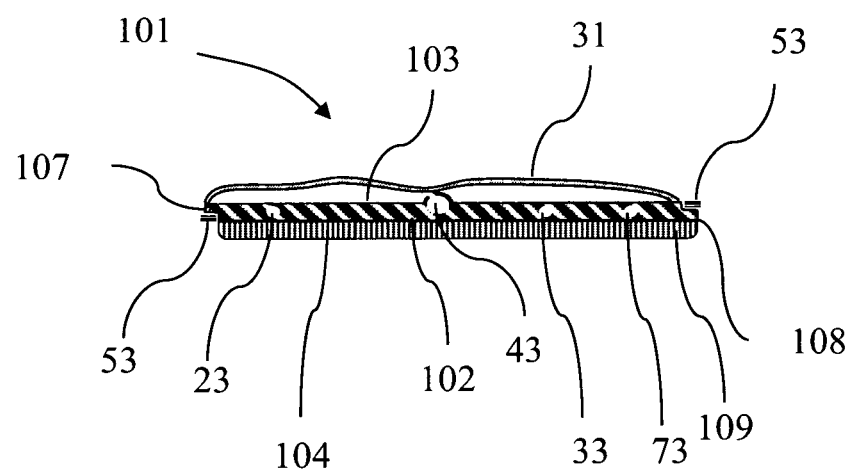
FIG. 5 is a sectional view of the device shown in FIG. 2 taken along plane 4-4.

As it is depicted in FIGS. 3, 4 and 5, fluid conduit 43 may be carried by sheet 101 along entire length of sheet 101 and proximally extends beyond strip 109 at proximal end portion 104 of sheet 101 in the form of a fluid conduit catheter 44 (FIG. 2) that terminates in a fluid conduit connection piece 45 that may be used to connect fluid conduit catheter 44 to an inflation or deflation device. Fluid conduit 43 may terminate distally in a fluid conduit port 41 at distal end portion 16 of overtube 11 (shown in FIG. 11). Fluid conduit 43 may be used to inflate or deflate examination compartment 95 with water or air.

As it is depicted in FIG. 5, an inflatable band 31 on face 103 of sheet 101, may extend across the entire width of sheet 101 at proximal end portion 104 of sheet 101 to form an inflatable sealing band 32 (FIG. 14) on the internal surface 13 of flexible overtube 11.

As it is depicted in FIG. 6, the inflatable band 31 may be located on face 103 of sheet 101 at proximal end portion 104 of sheet 101. On face 102, there may be strip 109 disposed at proximal end portion 104 of sheet 101 and catheter port projection 64 projects over strip 109.

Figure 7:
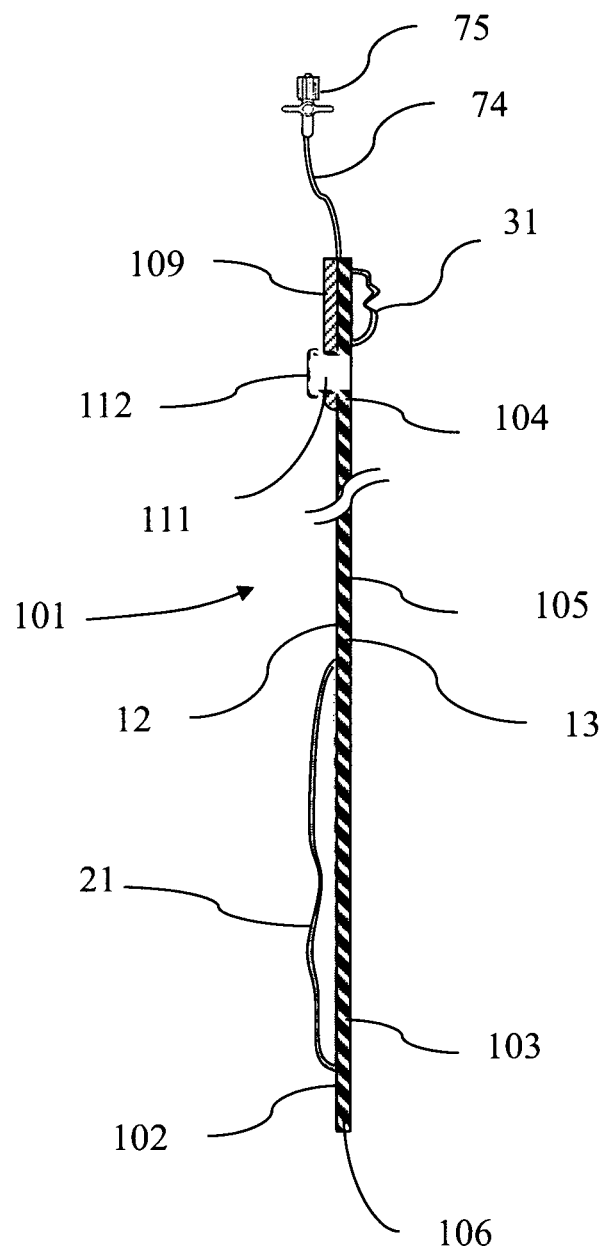
FIG. 7 is a longitudinal sectional view of the device shown in FIG. 2 taken along plane 6-6.

As it is depicted in FIG. 7, inflatable band 31 on face 103 of the sheet 101 at proximal end portion 104 of sheet 101 may be located proximal the irrigation port 111. Irrigation port 111 projects over strip 109 and may be capped by the irrigation port cap 112.

Figure 8:
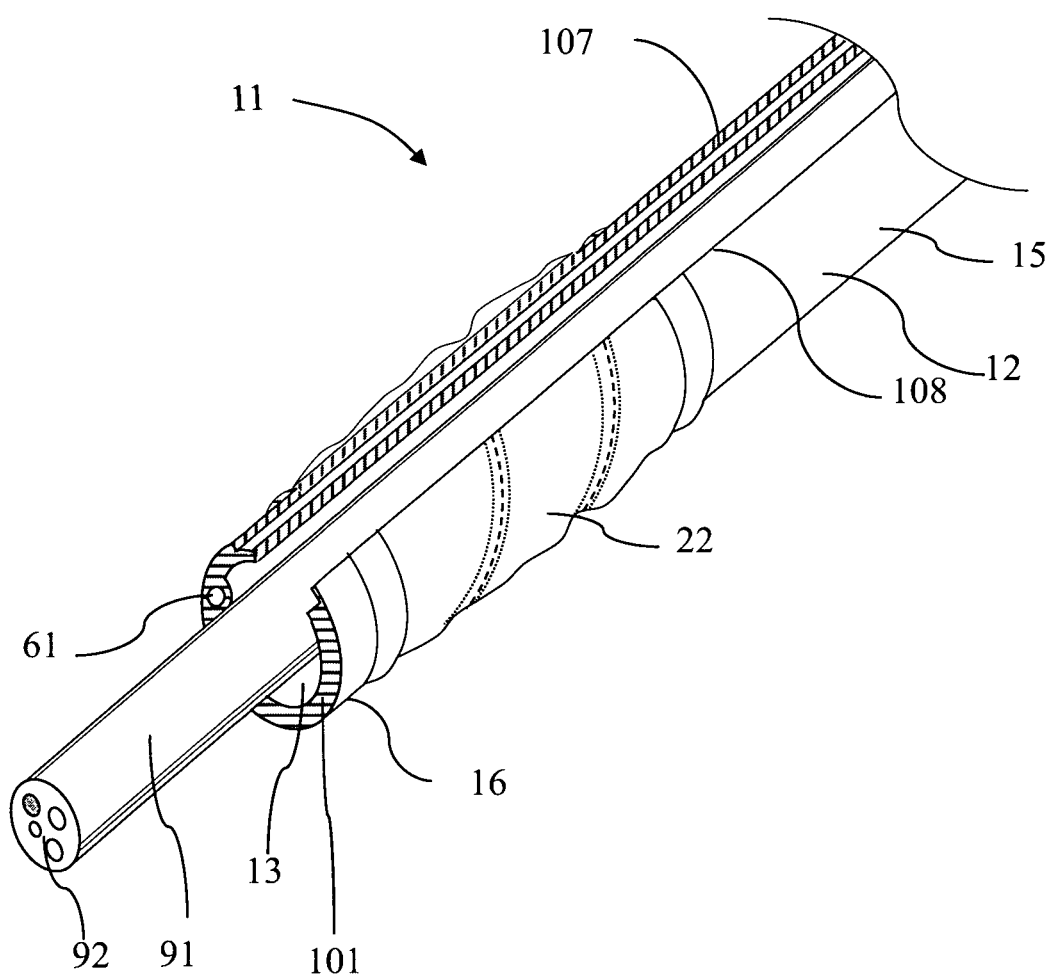
FIG. 8 is a schematic illustration of the endoscope accessory after placement of the endoscope shaft.

As it is depicted in FIG. 8, sheet 101 may envelop endoscope shaft 91 while opposed longitudinal edge portions 107 and 108 are still apart. When opposed longitudinal edge portions 107 and 108 coact, longitudinal seam 51 assembles (FIG. 9) along a portion or along entire length of flexible overtube 11.

Figure 9:
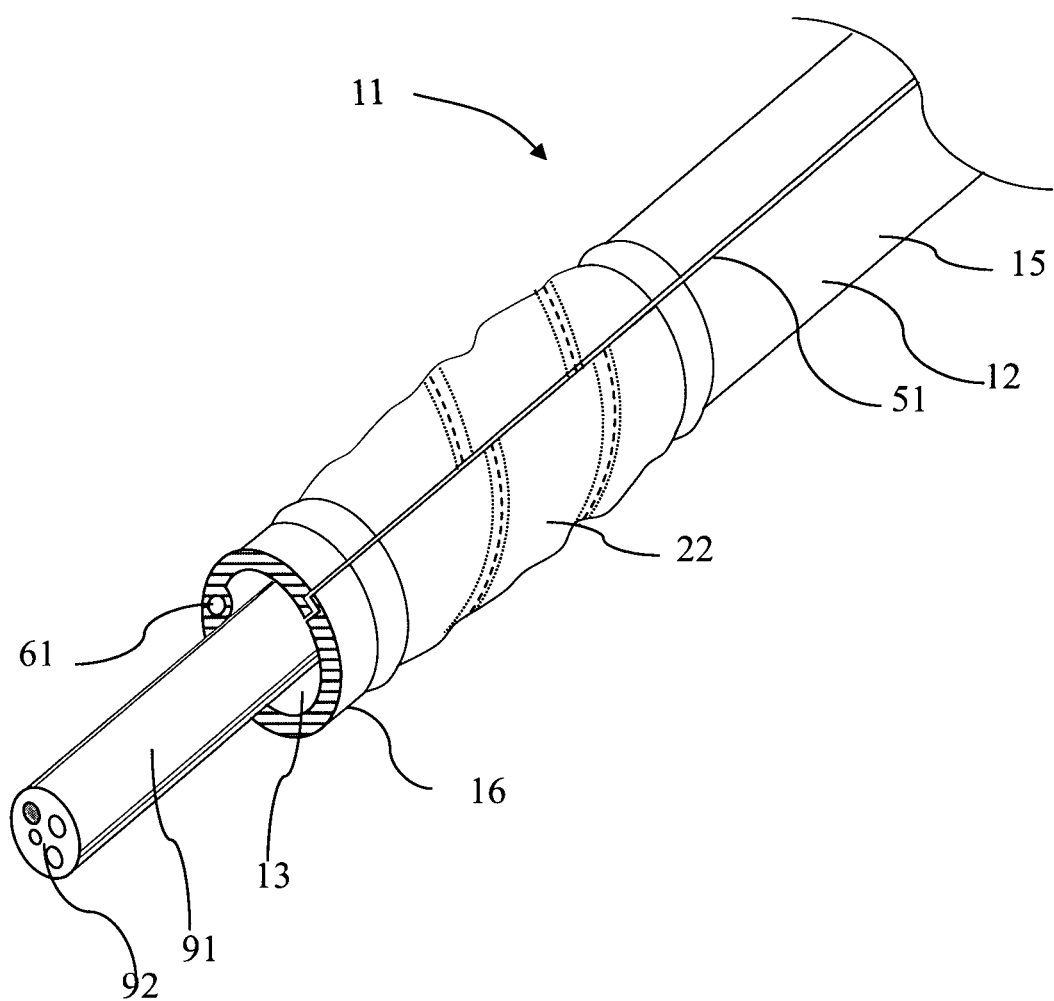
FIG. 9 is a schematic illustration of the endoscope accessory after placement of the endoscope shaft and closure of the longitudinal seam.

As it is depicted in FIG. 9, after longitudinal seam 51 assembles, overtube 11 forms around endoscope shaft 91. The overtube has an external surface 12 and an internal surface 13.

Figure 10:
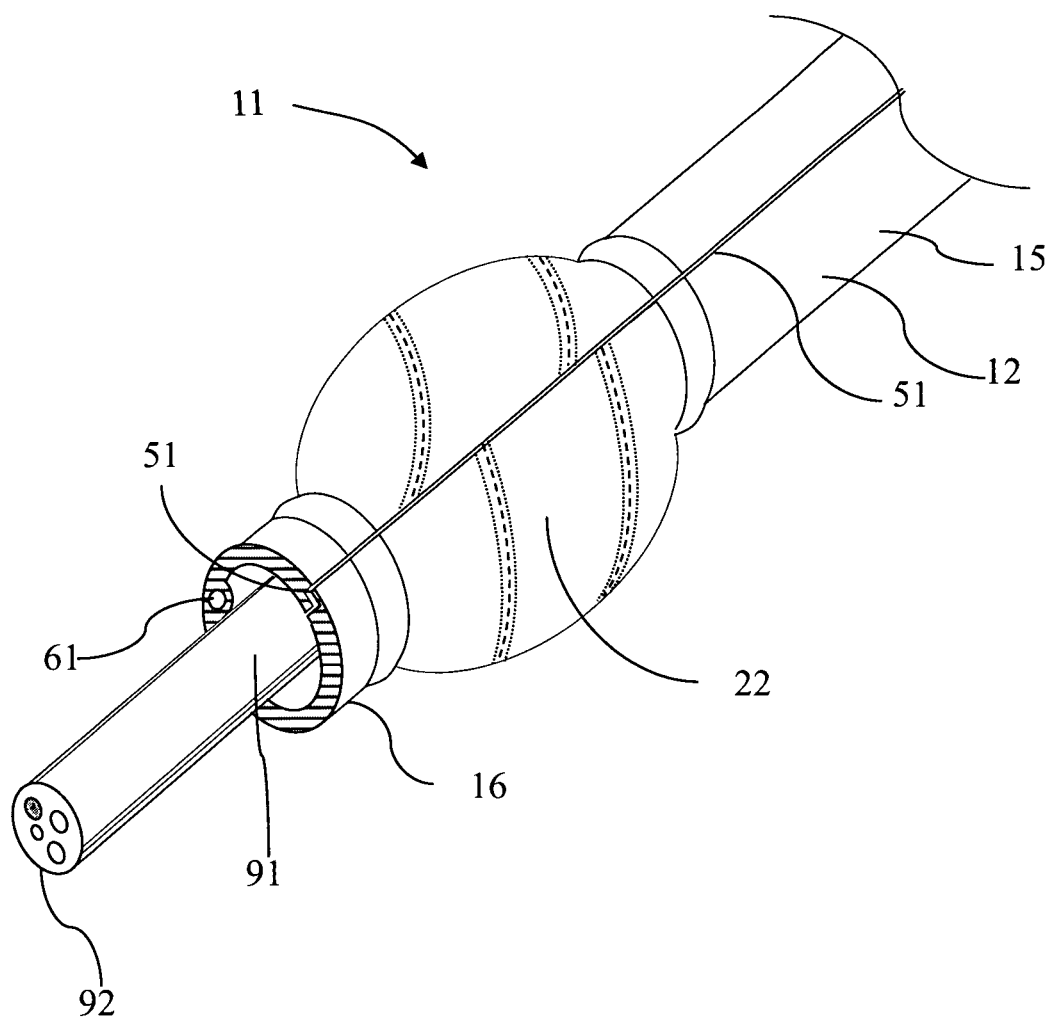
FIG. 10 is a schematic illustration of the endoscope accessory after placement of the endoscope shaft, closure of the longitudinal seam and inflation of the inflatable positioning ring.

As it is depicted in FIG. 10, inflatable positioning ring 22 disposed at distal end portion 16 of overtube 11 may be inflated.

Figure 11:
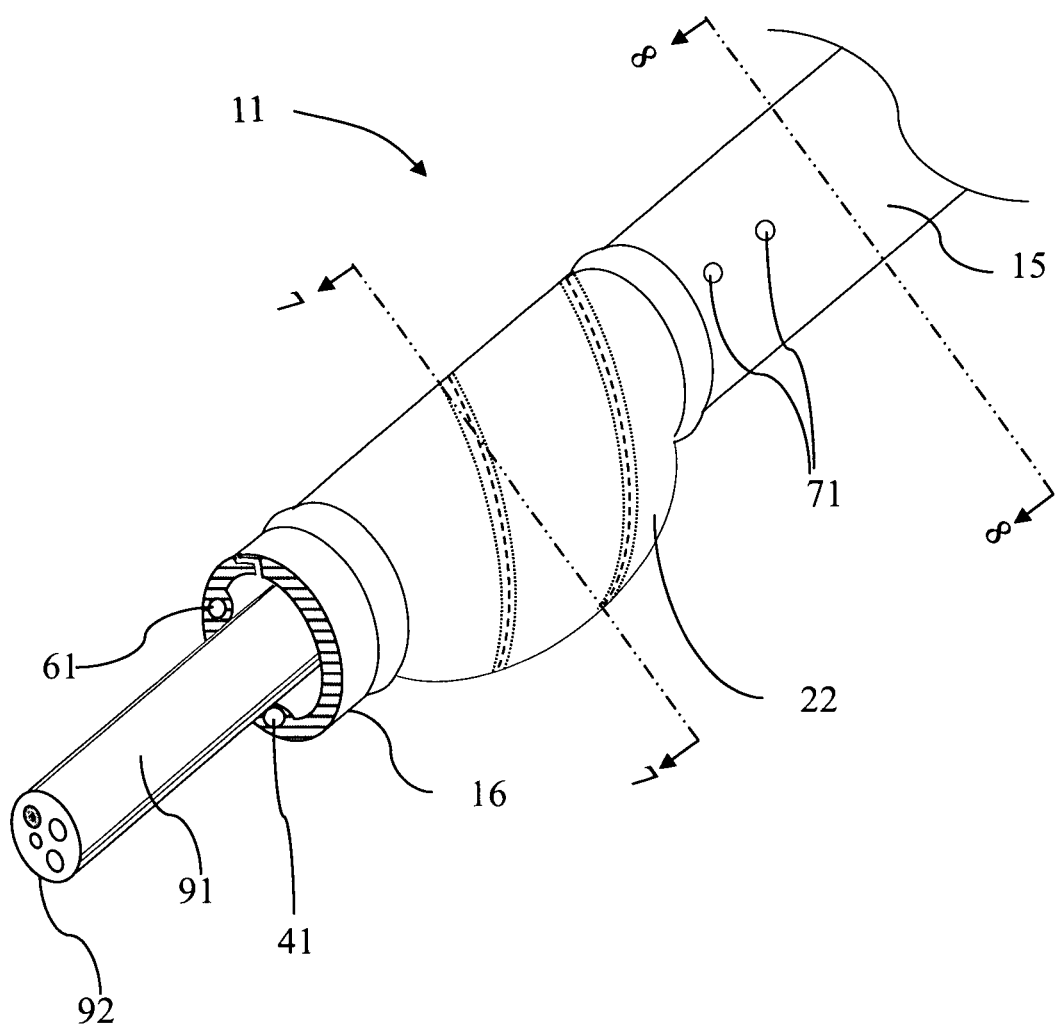
FIG. 11 is another schematic illustration of the endoscope accessory from different perspective after placement of the endoscope shaft, closure of the longitudinal seam and inflation of the inflatable positioning ring.

As it is depicted in FIG. 11, inflated positioning ring 22 may be asymmetric.

Figure 12:
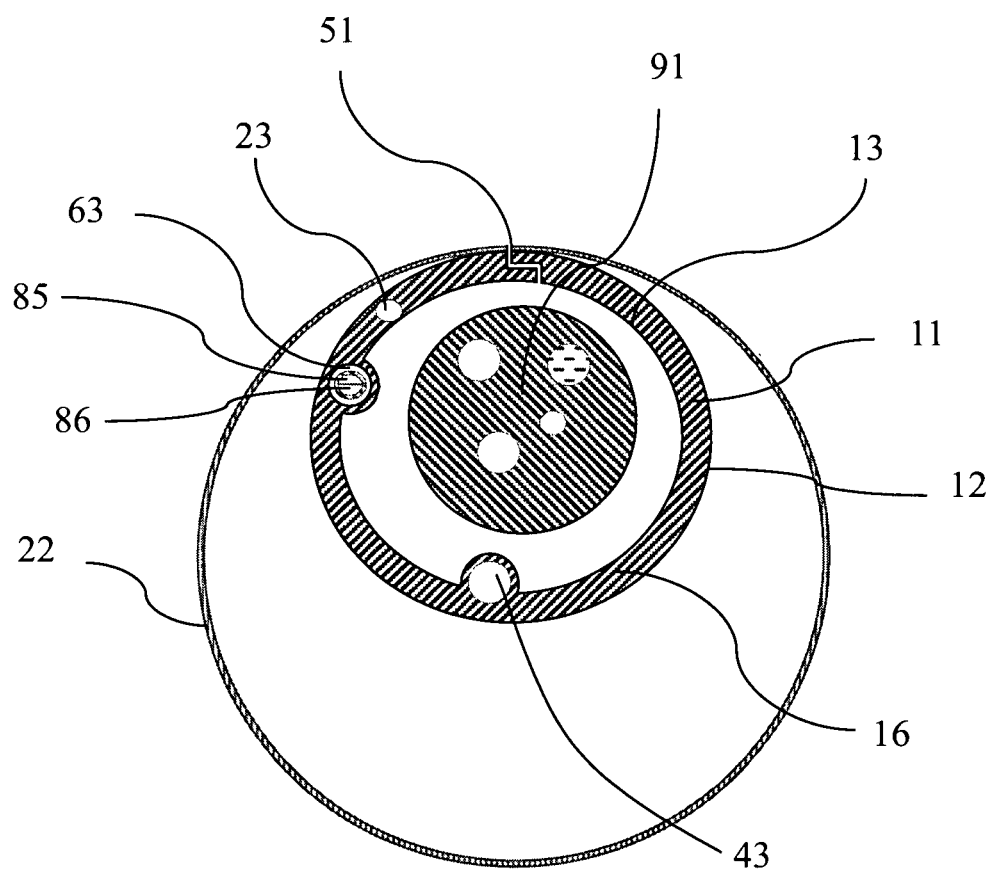
FIG. 12 is a sectional view of the device shown in FIG. 11 taken along plane 7-7.

FIG. 12 also shows that inflated positioning ring 22 may be eccentric relative to longitudinal axis of overtube 11 in a way that inflatable positioning ring 22 and overtube external surface 12 create internal tangent circles. The tangent point of these two circles may be at longitudinal seam 51. This allows better sealing created by inflatable positioning ring 22 within the gastrointestinal lumen and also creates an eccentric position for endoscope shaft 91 within the gastrointestinal lumen. This eccentric position of endoscope shaft 91 within the gastrointestinal lumen provide an advantage in maneuverability of endoscope tip 92 within examination compartment 95 in the gastrointestinal lumen particularly when overtube 11 is rotated.

Figure 13:
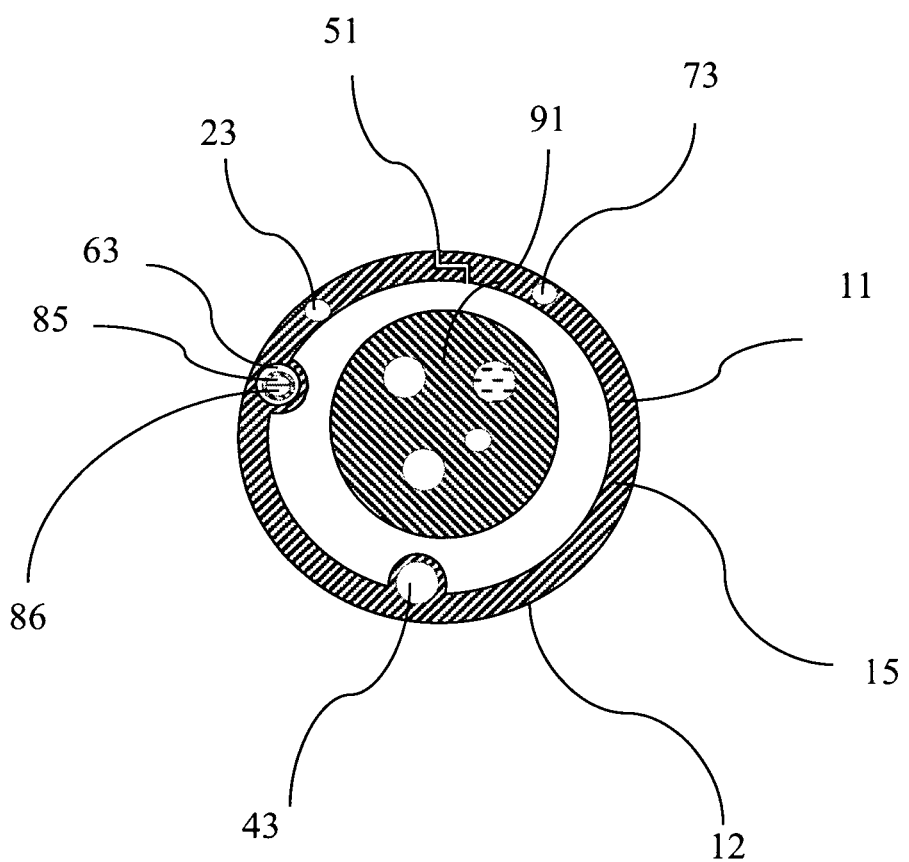
FIG. 13 is a sectional view of the device shown in FIG. 11 taken along plane 8-8.

As depicted in FIG. 13, overtube 11 may carry positioning ring inflation tube 23 that connects distally to inflatable positioning ring 22 (FIG. 12) and may proximally extends beyond handle 19 at the proximal end portion 14 of overtube 11 in the form of an external positioning ring inflation catheter 24 that terminates in a positioning ring inflation stopcock valve 25 (FIG. 1) that may be used to inflate or deflate inflatable positioning ring 22.

Another tube that may be carried by overtube 11 at its midportion 15 is suction conduit 73. Suction conduit 73 may terminates distally at a suction conduit port 71 (shown in FIGS. 1 and 11) and proximally extends beyond handle 19 at proximal end portion 14 of overtube 11 as an external suction conduit catheter 74 that terminates in a suction conduit connection piece 75 that may be used to connect external suction conduit catheter 74 to a suction device. After opposed longitudinal edge portions 107 and 108 coact to form a flexible overtube 11, suction conduit 73 may be used to drain air or water from the body cavity accumulated proximal to positioning ring 22.

Figure 14:
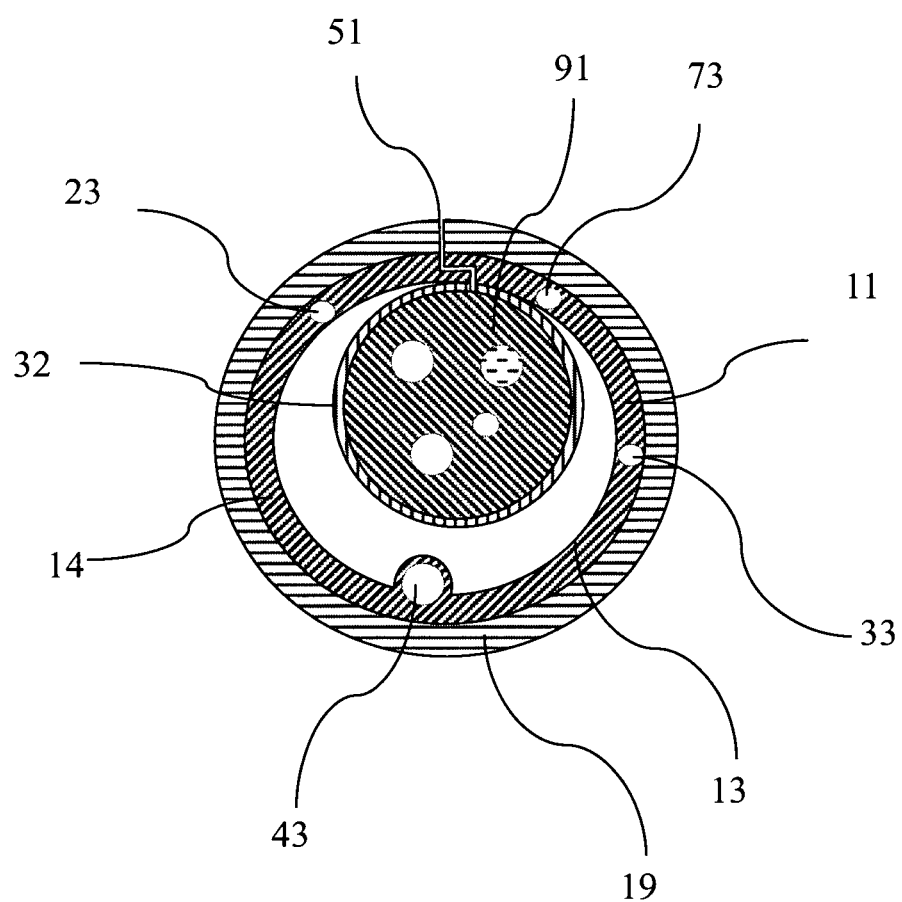
FIG. 14 is a sectional view of the device shown in FIG. 1 taken along plane 1-1.

As depicted in FIG. 14, inflated sealing band 32 may be eccentric relative to longitudinal axis of overtube 11 in a way that inflatable sealing band 32 and overtube internal surface 13 create internal tangent circles. The tangent point of these two circles may be at longitudinal seam 51. This allows a better sealing created by inflatable sealing band 32 over endoscope shaft 91.

Figure 28:
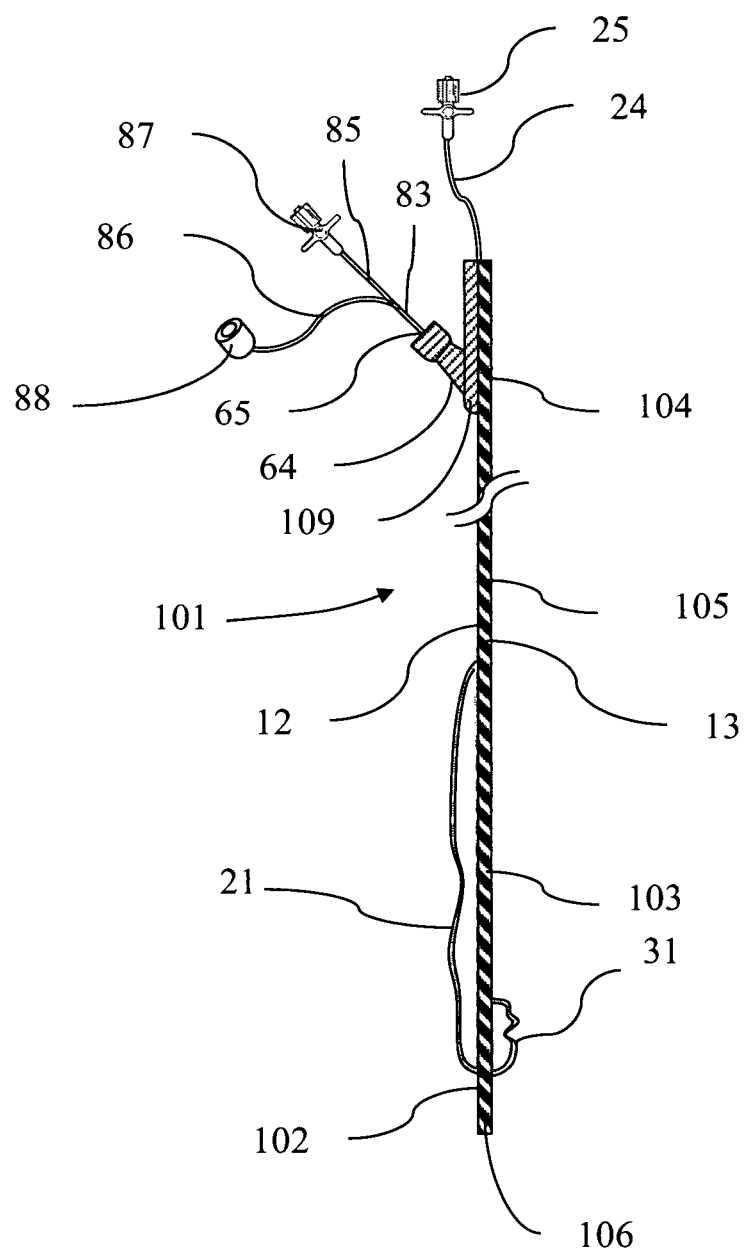
FIG. 28 is a longitudinal sectional view of the device shown in FIG. 2 taken along plane 5-5 showing the sealing band as a balloon that is located at the distal end portion of the overtube.

In alternate embodiment, as depicted in FIG. 28, sealing band 32 may be located and then inflated at the distal end portion of overtube 11 over endoscope shaft 91, thereby creating a seal at distal end of overtube 11.

Figure 29:
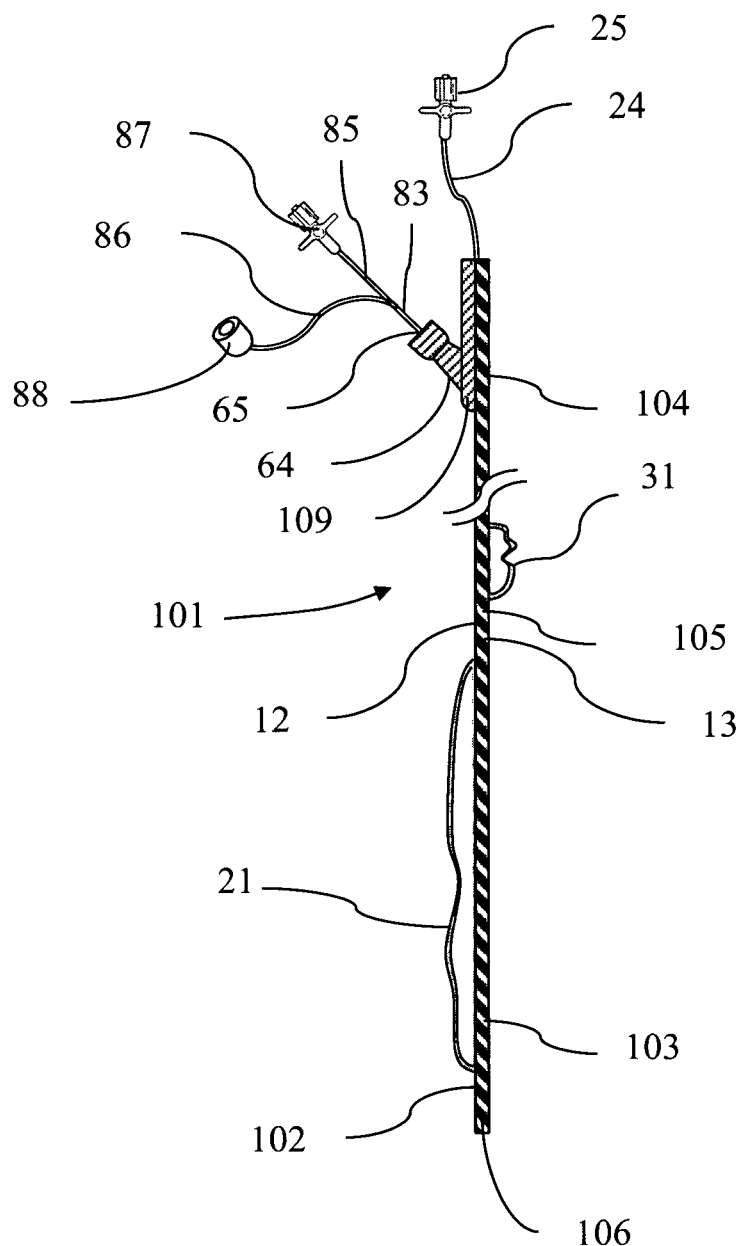
FIG. 29 is a longitudinal sectional view of the device shown in FIG. 2 taken along plane 5-5 showing the sealing band as a balloon that is located at the midportion of the overtube.

In another embodiment, as depicted in FIG. 29, sealing band 32 may be located and then inflated at the midportion of overtube 11 over endoscope shaft 91, thereby creating a seal at the midportion 15 of overtube 11. Those skilled in arts will quickly understand, sealing band 32 may be located at any point along the length of overtube 11.

Inflatable sealing band 32 may be inflated using a sealing band inflation tube 33 which communicate with sealing band inflation catheter 34 (FIG. 1). Overtube 11 carries sealing band inflation tube 33 that communicate with inflatable sealing band 32 on one end and proximally extends beyond handle 19 at the proximal end portion 14 of overtube 11 in the form of external sealing band inflation catheter 34 (FIG. 1). External sealing band inflation catheter 34 may terminate in a sealing band inflation stopcock valve 35 that may be used to inflate or deflate inflatable sealing band 32.

Figure 15:
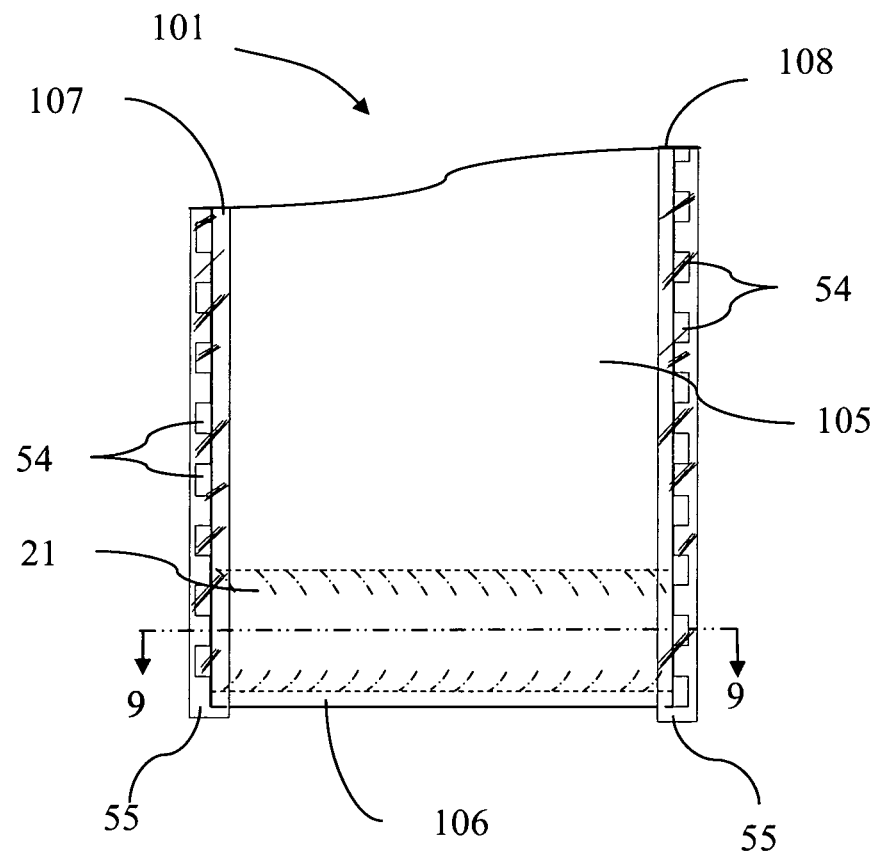
FIG. 15 is a partial plan view of the present invention showing spaced magnets and magnet covers at the longitudinal edge portions.
Figure 16:
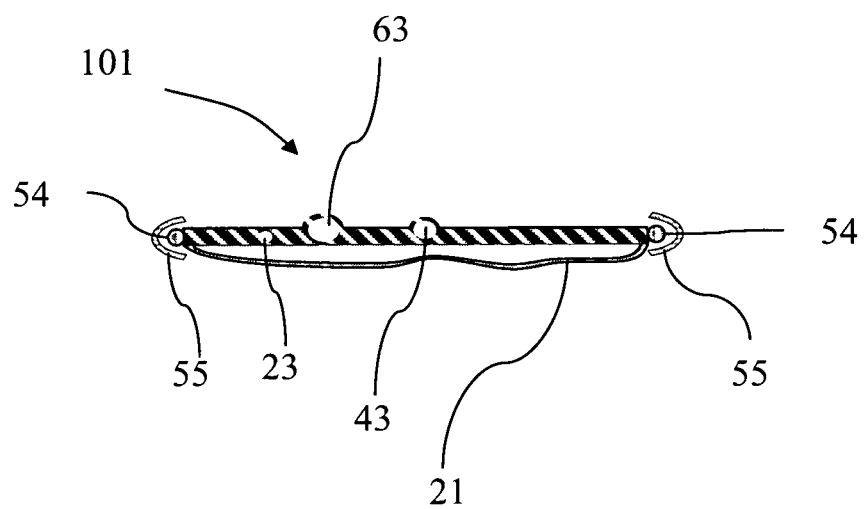
FIG. 16 is a sectional view of the present invention showing spaced magnets and magnet covers at the longitudinal edge portions taken along plane 9-9.

An alternative embodiment of sheet 101 is depicted in FIGS. 15 and 16. The closure may include a plurality of spaced magnets 54 are provided in lieu of adhesive 52 and release sheet 53, carried by each longitudinal edge portions 107 and 108 along entire length of sheet 101 for coacting with the opposed edge portion. Spaced magnets 54 on longitudinal edge portions 107 are interspersed with spaced magnets 54? on longitudinal edge portion 108. The inflatable pocket 21 and the inflatable band 31 are offset from magnets 54. To avoid activation of the magnet before placing endoscope shaft 91 within sheet 101, longitudinal edge portions 107 and 108 may be supplied with a longitudinal slit sleeve magnet cover 55. Magnets 54 may coact with the opposed longitudinal edge portion magnets 54 when magnet covers 55 are removed from longitudinal edge portions 107 and 108.

Figure 17:
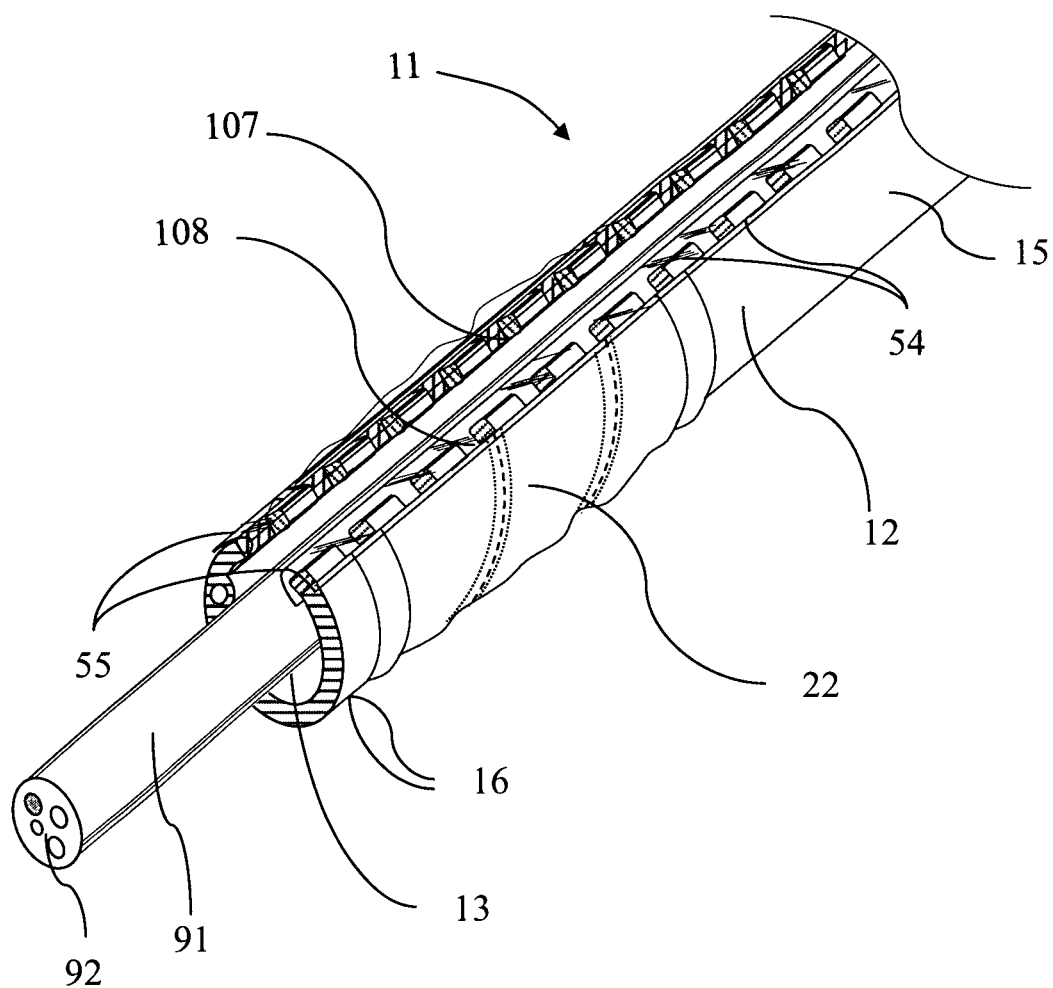
FIG. 17 is a partial schematic illustration of the endoscope accessory showing spaced magnets and magnet covers at the longitudinal edge portions.

As it is depicted in FIG. 17, sheet 101 may wrap around or envelop endoscope shaft 91 while opposed longitudinal edge portions 107 and 108 are still apart. Magnets 54 cannot coact with the opposed longitudinal edge portion magnets while magnet covers 55 are covering magnets 54 supplied at longitudinal edge portions 107 and 108.

Figure 18:
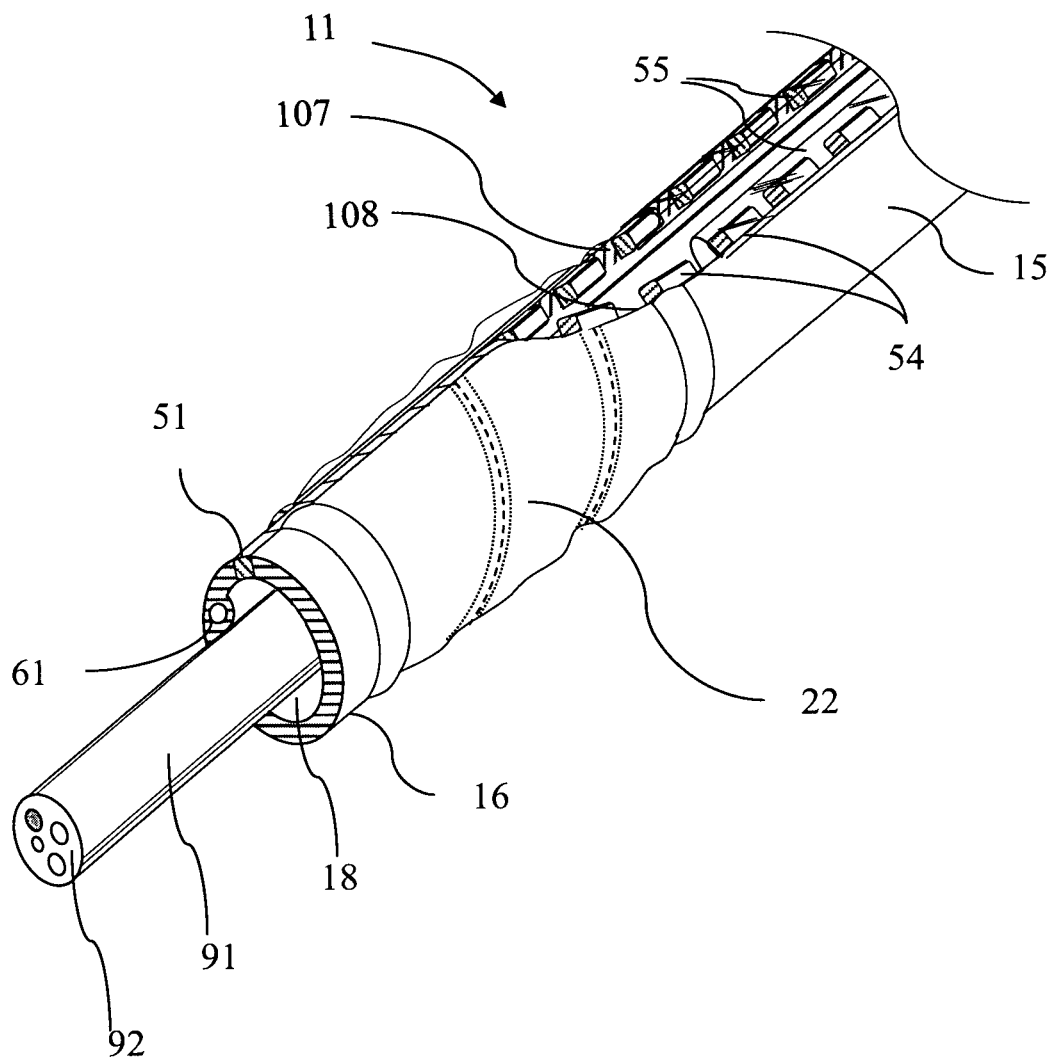
FIG. 18 is a partial schematic illustration of the endoscope accessory showing spaced magnets and magnet covers at the longitudinal edge portions after placement of the endoscope shaft and partial closure of the longitudinal seam.

As it is depicted in FIG. 18, when magnet cover 55 is removed partially by pulling magnet cover 55 proximally, distal end portion 16 of overtube 11 magnets 54 at opposed longitudinal edge portions 107 and 108 are exposed. Exposed magnets 54 assemble longitudinal seam 51 starting from distal end portion 16 of overtube 11. Repeating this sequence closes longitudinal seam 51 along entire length of flexible overtube 11 and overtube 11 forms around endoscope shaft 91.

Figure 19:
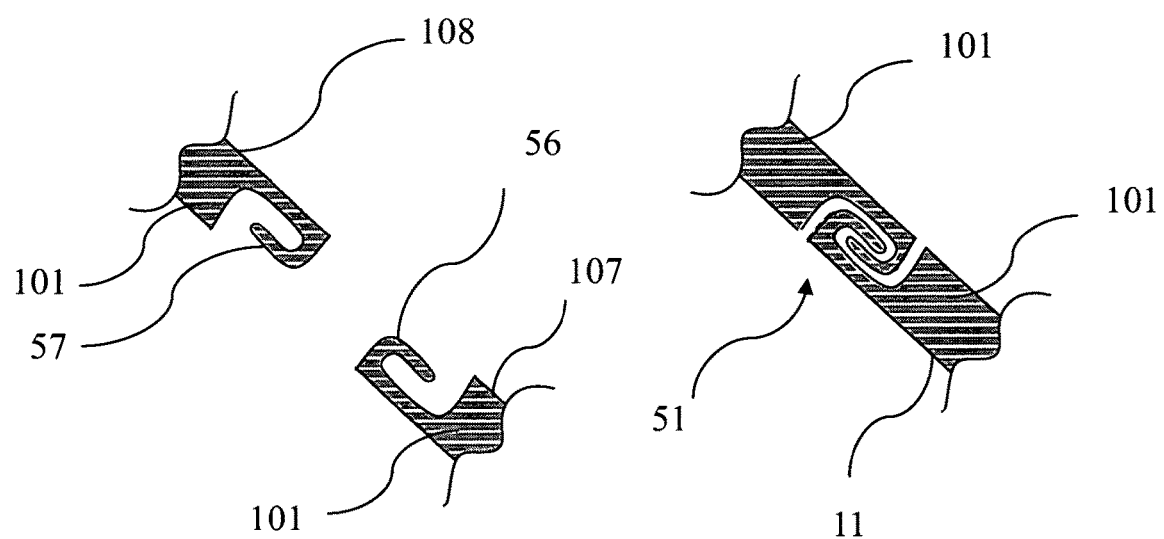
FIG. 19 is a partial sectional view of the present invention showing tongue and groove mechanism at the longitudinal edge portions.

A further alternative embodiment of sheet 101 is depicted in FIG. 19 depicting a closure that includes cooperating coupling structures 56 and 57 are provided in lieu of adhesive 52 and release sheet 53, carried by each longitudinal edge portions 107 and 108 along entire length of sheet 101. The cooperating coupling structures 56 and 57 may provide an interlocking closure mechanism in a tongue and groove format and allows a reversible closure or release of longitudinal seam 51 along the entire length of overtube 11 (not shown).

Figure 20:
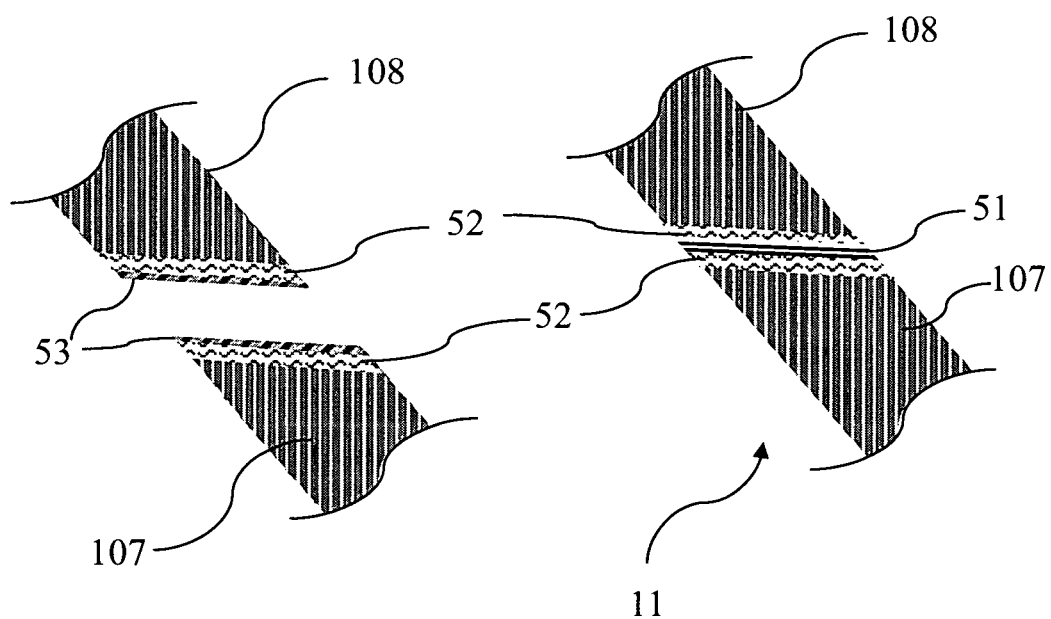
FIG. 20 is a partial sectional view of the present invention showing beveled edges at the longitudinal edge portions.

Yet another embodiment of sheet 101 is depicted in FIG. 20. In this configuration, the closure includes longitudinal edge portions 107 and 108 are beveled in angles that complement the opposed edge portion angle. Edge portions 107 and 108 are situated side by side so as to not overlap each other. The beveled edges of the opposed longitudinal edge portions 107 and 108 may be supplied with an adhesive 52 covered by a release sheet 53. After removal of release sheet 53 from adhesive 52 at the beveled edges of opposed longitudinal edge portions 107 and 108, the edges are adhered to form a liquid tight seam 51 along entire length of overtube 11 (not shown).

Figure 21A:
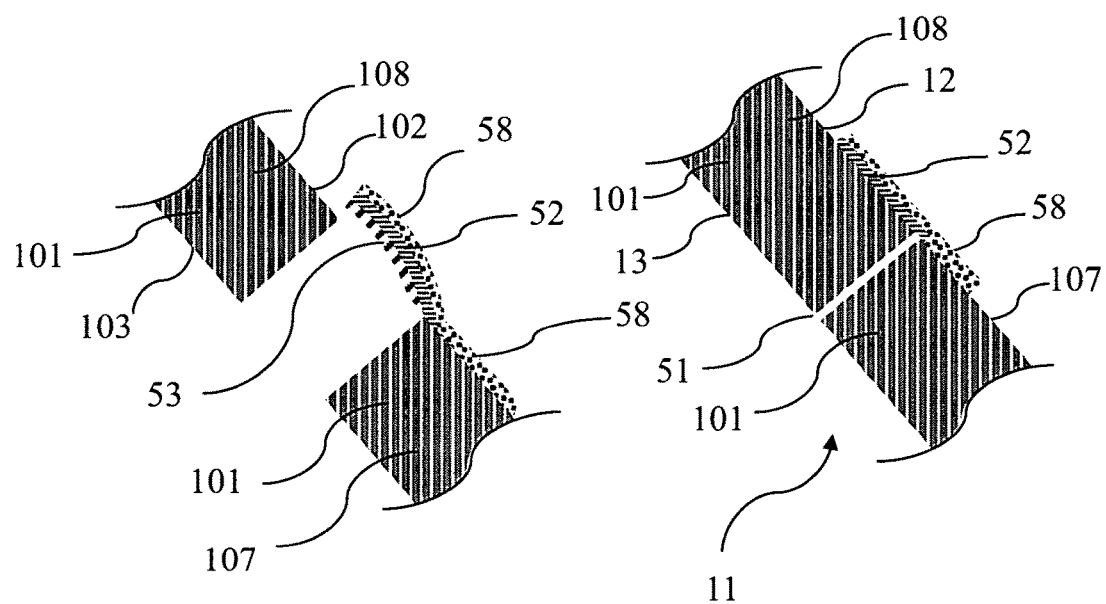
FIGS. 21A and 21B are partial sectional views of the present invention showing an elongated flap at the longitudinal edge portions.

Another embodiment of sheet 101 is depicted in FIG. 21A. In this configuration, each edge portion of longitudinal edge portions 107 and 108 are either straight or beveled (not shown) in angles that complement the opposed edge portion angle and the edges are situated side by side and so as to not overlap each other. Edge portion 107 is supplied with an elongated sheet 58 along entire length of sheet 101 on face 102. Sheet 58 acts as a flap and may be permanently attached half of its width along entire length, over face 102 of edge portion 107 of sheet 101. The other half of the width of flap 58 is not attached and can be supplied with an adhesive 52 covered by a release sheet 53 along entire length. After removal of the release sheet 53 from adhesive 52, the unattached half of flap 58 may be adhered to face 102 of opposed edge portion 108 of sheet 101 to form a liquid tight seam 51 covered with a strip of adhesive on outer surface 12 along entire length of overtube 11 (not shown).

In an alternative configuration, sheet 101 may be composed of silicone rubber sheet material and the flap 58 with covered adhesive 52 and release sheet 53 may be replaced with a self-fusing silicone tape 59 covered by a release sheet 53 (not shown).

Figure 21B:
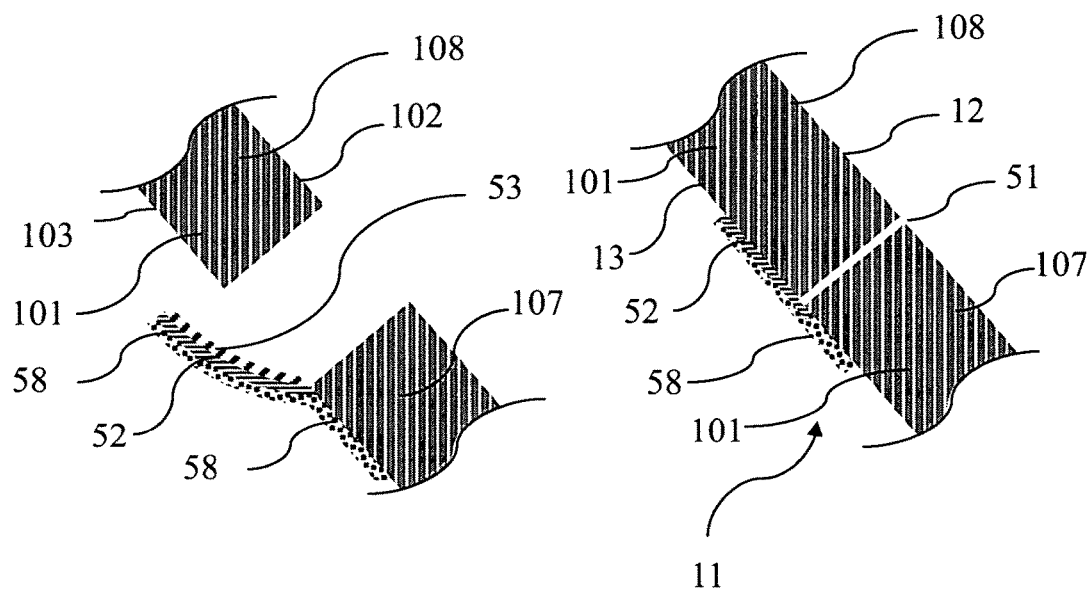

Another embodiment of sheet 101 is depicted in FIG. 21B. In this configuration, each edge portion of longitudinal edge portions 107 and 108 are either straight or beveled (not shown) in angles that complement the opposed edge portion angle and the edges are situated side by side and so as to not overlap each other. Edge portion 107 is supplied with an elongated sheet 58 along entire length of sheet 101 on face 103. Sheet 58 acts as a flap and may be permanently attached half of its width along entire length, over face 103 of edge portion 107 of the sheet 101. The other half of the width of flap 58 is not attached and can be supplied with an adhesive 52 covered by a release sheet 53 along entire length. After removal of release sheet 53 from adhesive 52, the unattached half of flap 58 may be adhered to face 103 of opposed edge portion 108 of sheet 101 to form a liquid tight seam 51 covered with a strip of adhesive on the inner surface 13 along entire length of overtube 11 (not shown). In an alternative configuration, sheet 101 is composed of silicone rubber sheet material and flap 58 with covered adhesive 52 and release sheet 53 may be replaced with a self-fusing silicone tape 59 covered by a release sheet 53 (not shown).

Figure 22A:
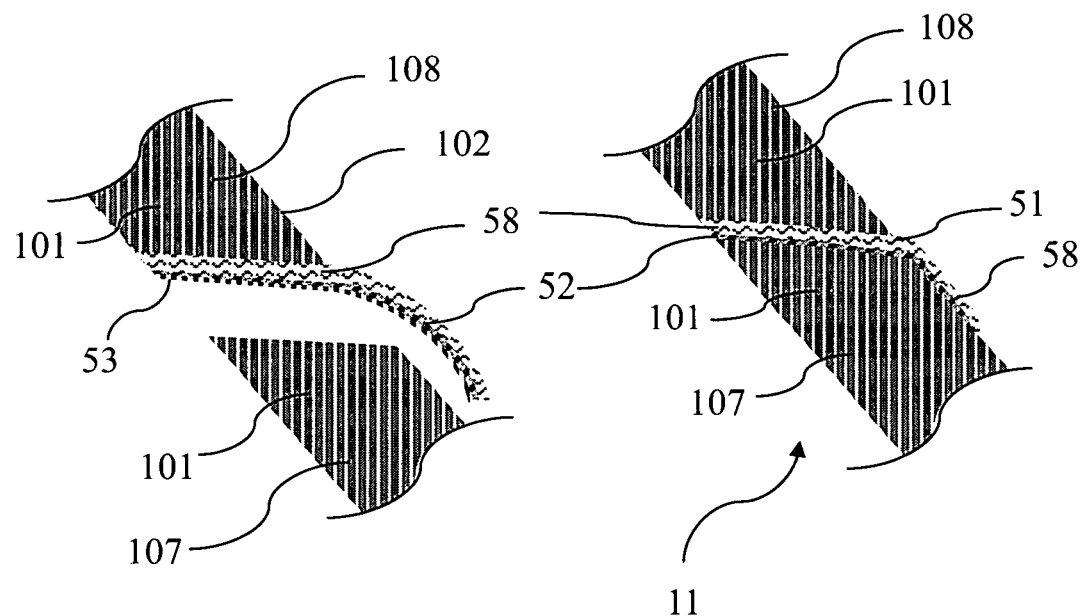
FIG. 22A is a partial sectional view of the present invention showing an elongated flap at the longitudinal edge portions.

Another embodiment of sheet 101 is depicted in FIG. 22A. In this configuration, each edge portion of longitudinal edge portions 107 and 108 are either straight (not shown) or beveled in angles that complement the opposed edge portion angle and the edges are situated side by side and so as to not overlap each other. Edge portion 108 is supplied with an elongated sheet 58 along entire length of sheet 101 on edge. Sheet 58 acts as a flap and is permanently attached half of its width along entire length, over edge portion 108 of sheet 101. The other half of the width of flap 58 is not attached. Flap 58 may be supplied with an adhesive 52 covered by a release sheet 53 along entire length. After removal of release sheet 53 from adhesive 52, flap 58 can may adhere to opposed edge portion 107 as well as a portion of face 103 of opposed edge portion 107 of sheet 101 to form a liquid tight seam 51 along entire length of overtube 11 (not shown).

In alternative embodiment (not shown), adhesive flap 58 and adhesive tape 52 may extend over face 103 of edge portion 108 to provide more support for adhesion of opposed edge portion 108 and 107 adhesive flap to create seam 51.

Figure 22B:
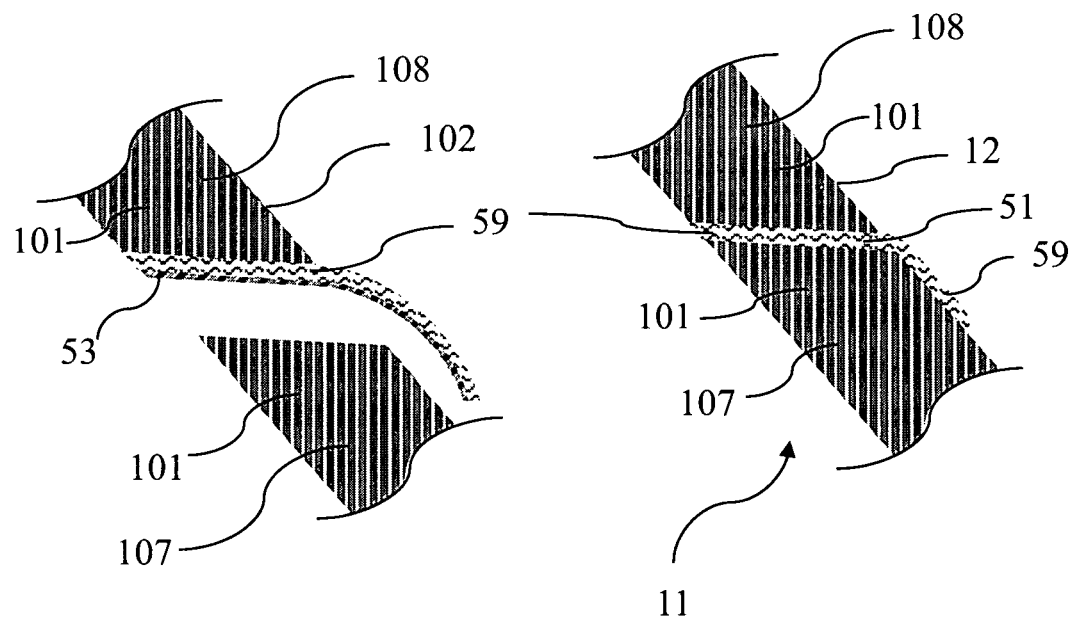
FIG. 22B is a partial sectional view of the present invention showing an elongated flap made from self-fusing silicone tape at the longitudinal edge portions.

Another embodiment of sheet 101 is depicted in FIG. 22B. In this configuration, sheet 101 may be composed of silicone rubber sheet material and edge portions 107 and 108 are either straight (not shown) or beveled in angles that complement the opposed edge portion angle. Edge portions 107 and 108 are situated side by side so as to not overlap each other. Longitudinal edge portions 108 may be supplied with a self-fusing silicone tape 59 covered by a release sheet 53. Self-fusing silicone tape 59 may be attached half of its width along entire length to beveled longitudinal edge portion 108 of sheet 101. The other half of the width of self-fusing silicone tape 59 is an unattached flap. After removal of release sheet 53 from the self-fusing silicone tape 59, edge portions 107 and 108 are adhered to form a liquid tight seam 51 along entire length of overtube 11 and the unattached half of self-fusing silicone tape 59 flap may be adhered to face 102 of opposed edge portion 107 of sheet 101 on outer surface 12 along entire length of overtube 11 (not shown).

In alternative embodiment (not shown), silicon tape 59 may extend over face 103 of edge portion 108 to provide more support for adhesion of opposed edge portion 108 and 107 using self-fusing tape 59 to create seam 51.

Figure 23:
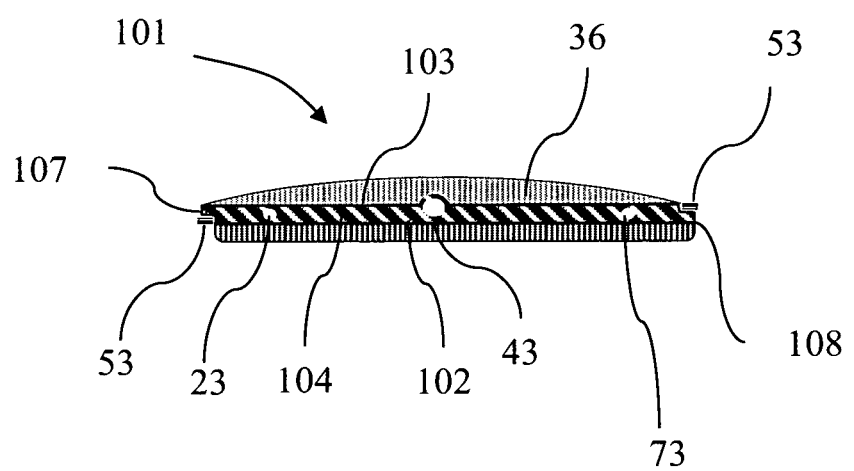
FIG. 23 is a sectional view of the present invention showing an elastomeric bead taken along plane 3-3.
Figure 24:
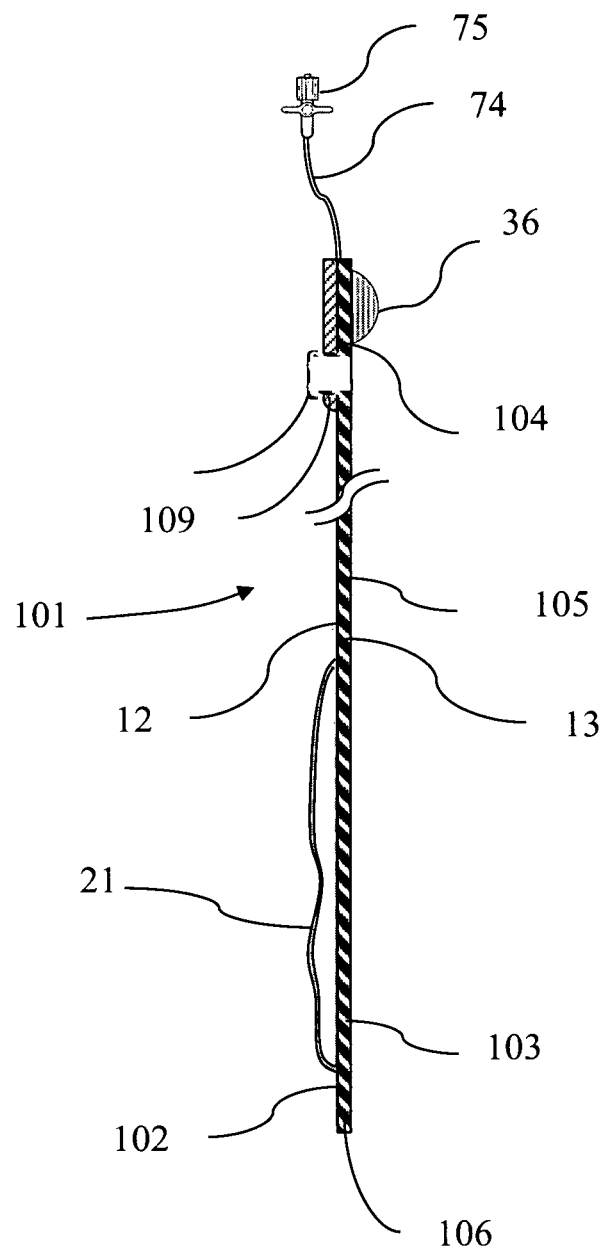
FIG. 24 is a longitudinal sectional view of the present invention showing the elastomeric bead taken along plane 6-6.

An alternative embodiment in sheet 101 is depicted in FIGS. 23 and 24. An elongated elastomeric bead 36 on face 103 of sheet 101 may be provided in lieu of inflatable pocket 31, extending across entire width of the sheet at proximal end portion 104 of sheet 101. Elastomeric bead 36 may form an elastomeric sealing bead on internal surface 13 of overtube 11 (not shown) when opposed longitudinal edge portions 107 and 108 coact to form overtube 11. Those skilled in arts will quickly understand, elastomeric bead 36 may be located at any point along the length of overtube 11.

Figure 30:
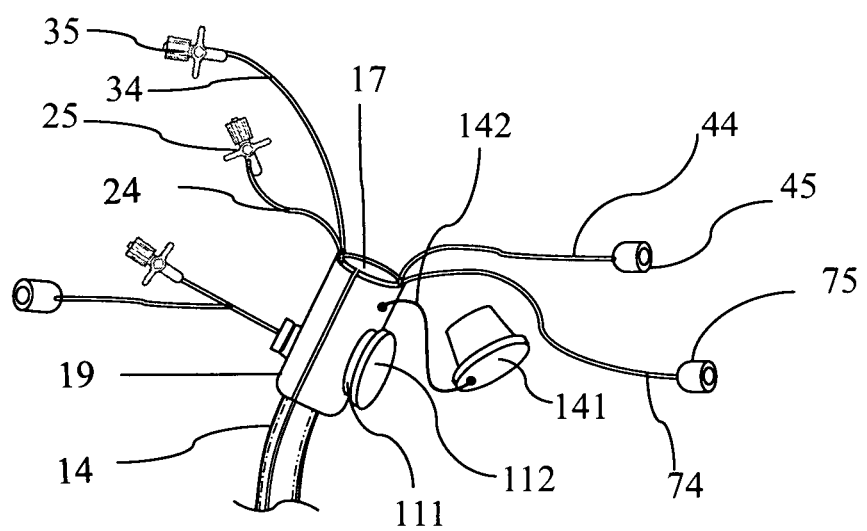
FIG. 30 is a perspective view of an alternate embodiment of the present invention depicting a proximal opening cap in an open position connected to a string at the proximal end of the overtube.
Figure 31:
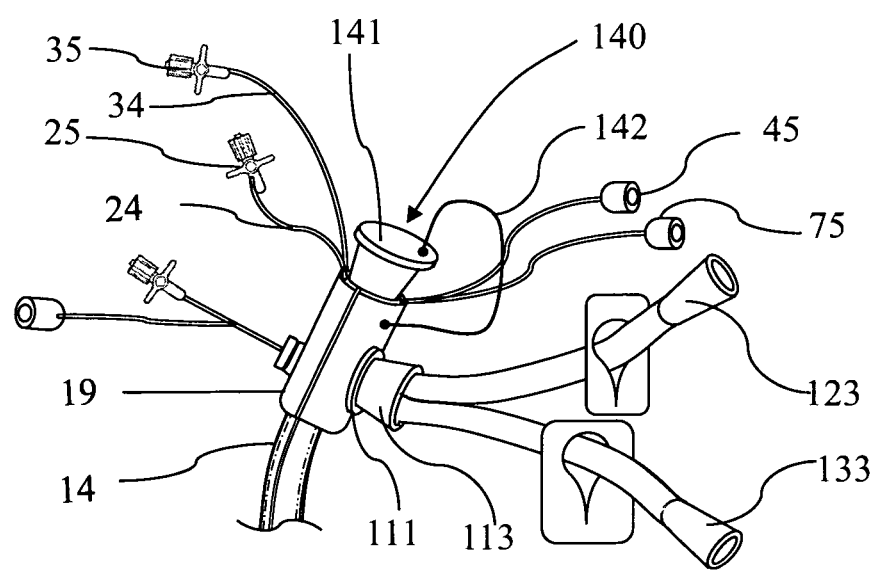
FIG. 31 is a perspective view of an alternate embodiment of the present invention depicting the proximal opening cap in a closed position at the proximal opening of the overtube.
Figure 32:
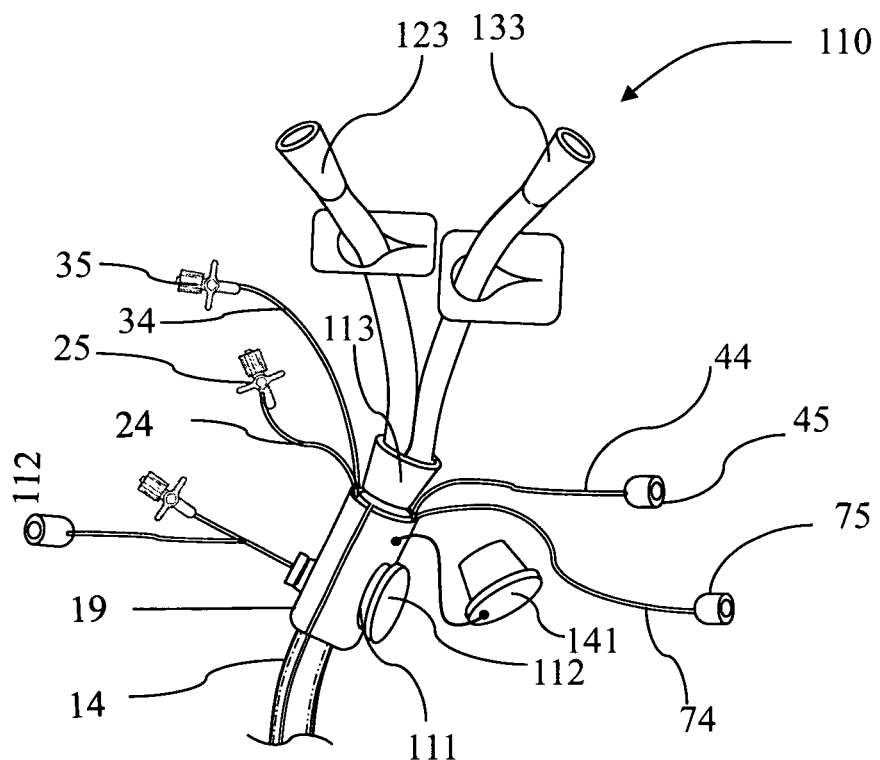
FIG. 32 is a perspective view of the proximal opening cap in an open position and the irrigation tube assembly is connected to the proximal opening of the overtube and the irrigation port is closed with the irrigation port cap.
Figure 33:
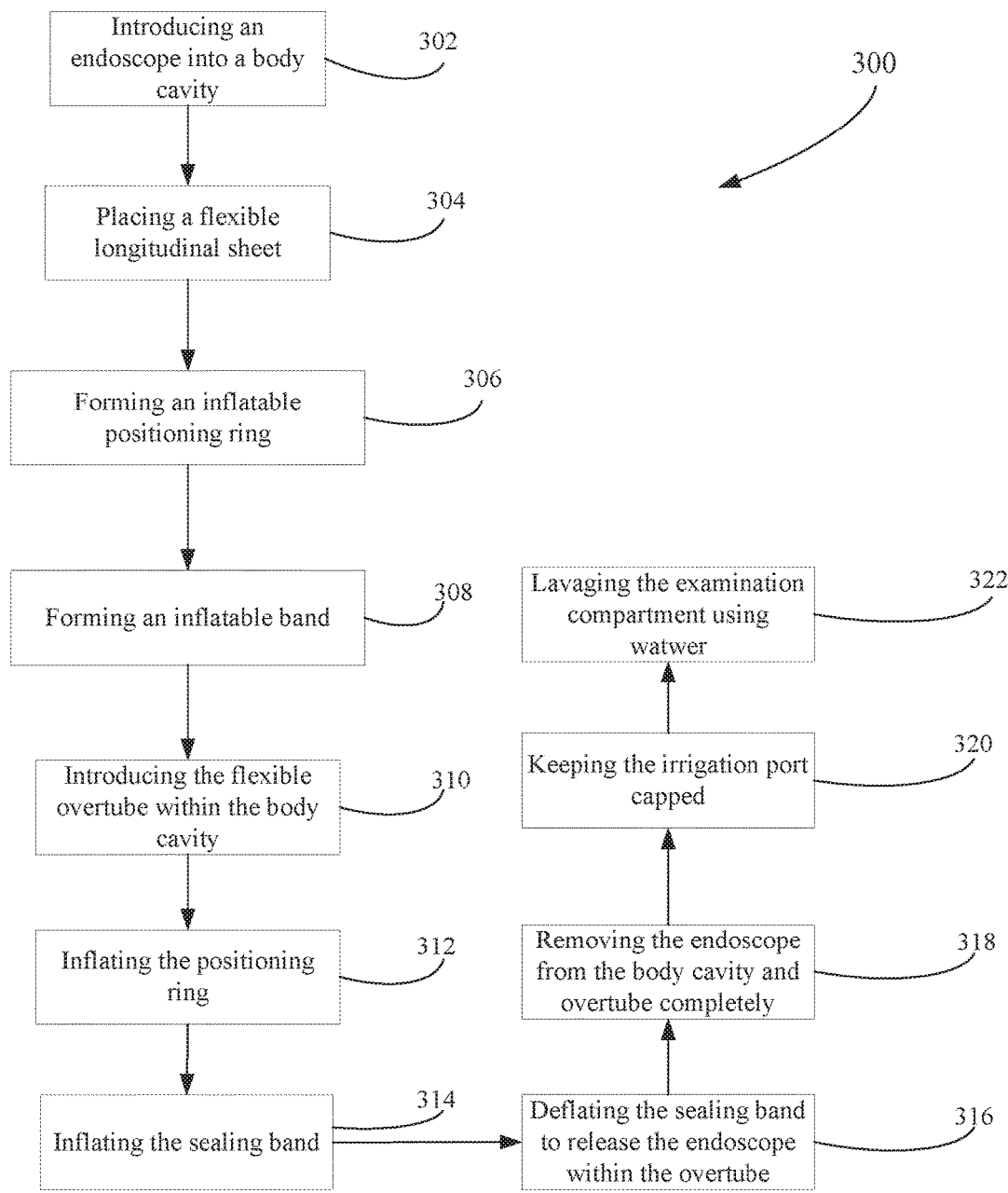
FIG. 33 is a flow chart illustrating an exemplary method for performing an endoscope procedure.
Figure 34:
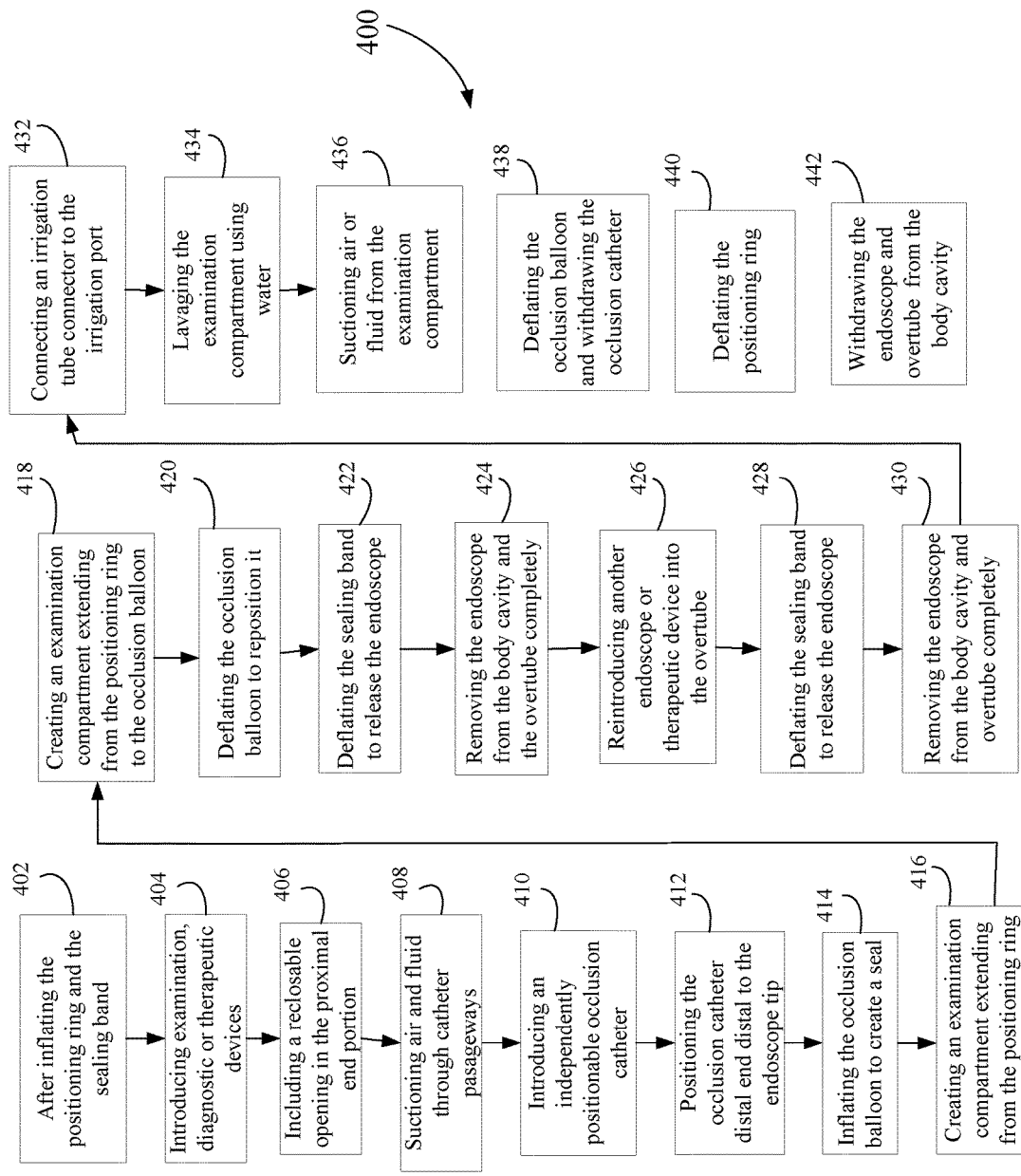
FIG. 34 is a flow chart illustrating additional steps of the method for performing an endoscope procedure.

An alternate embodiment, as depicted in FIGS. 30 and 31, may include a cap system 140, comprising a removable cap 141 and a string 142 that is connected from one end to cap 141 and on the other end to handle 19 at proximal end portion 14 of overtube 11. Cap 141 may be used to reversibly seal proximal opening 17 of overtube 11. Cap 141 may close the proximal opening 17 of overtube 11 when endoscope shaft 91 is not in overtube 11. As depicted in FIG. 30, cap 141 may be connected to overtube 11 by a string 142. Cap 141 may be positioned to close proximal opening 17 of overtube 11 and seal it (FIG. 31). Alternatively cap 141 may be an open position, as a separate member that is positioned out of the lumen of overtube 11 while still attached to string 142 (FIGS. 30 and 32). Those skilled in the arts will understand that string 142 is for convenience only and not critical to the invention. Cap 141 may be an independent feature, or, alternatively, may be attached to device 10 by any suitable means.

An alternative embodiment, as depicted in FIG. 32, irrigation system 110 may be connected to proximal opening 17 of overtube 11 when endoscope shaft 91 is not in overtube 11. In this configuration, irrigation port 111 is capped by irrigation port cap 112.

Figure 25:
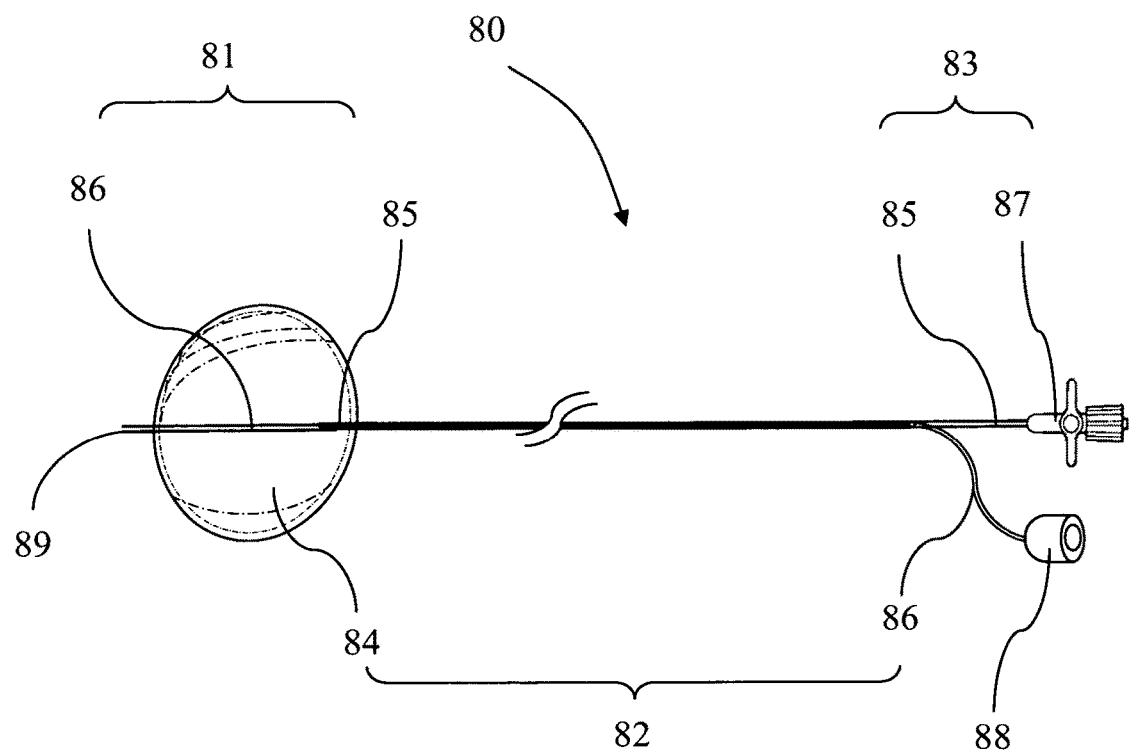
FIG. 25 is a schematic illustration of the occlusion balloon catheter.
Figure 26:
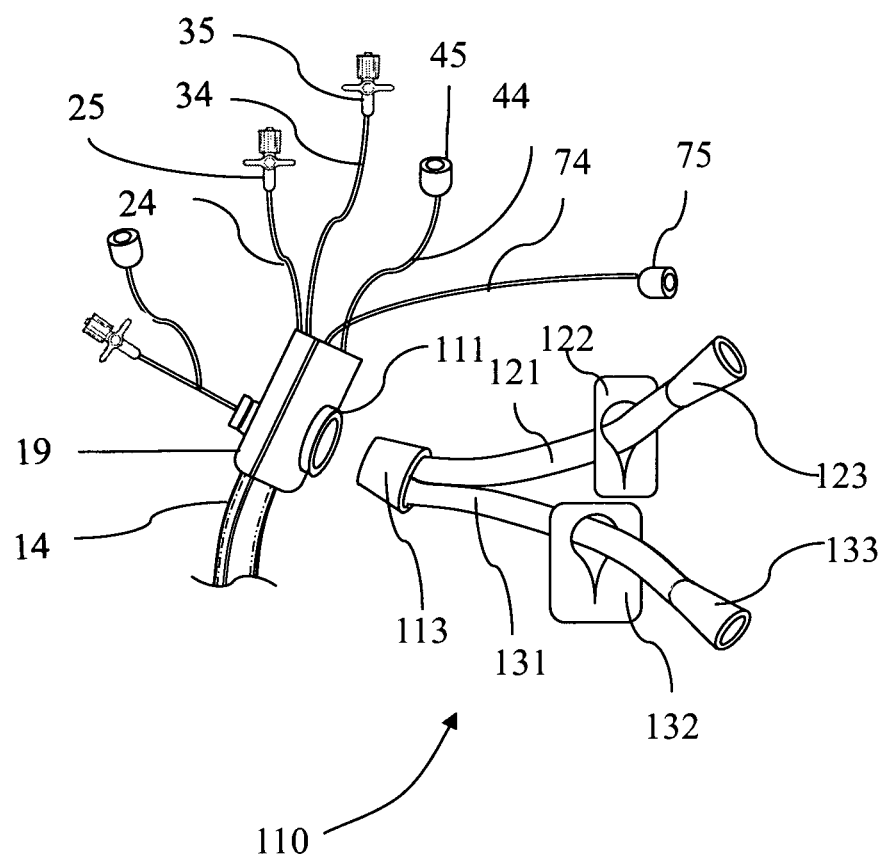
FIG. 26 is a partial schematic illustration of the proximal end portion of the endoscope accessory and the irrigation port tube system.

B—Catheter and Occlusion Balloon:

As it is depicted in FIG. 25, the occlusion balloon catheter 80 has a distal end portion 81, a midportion 82 and a proximal end portion 83. An occlusion balloon 84 is situated at distal end portion 81 of occlusion balloon catheter 80. Occlusion balloon 84 may be inflated by an occlusion balloon inflation tube 85 that may be carried by occlusion balloon catheter 80. An occlusion catheter suction tube 86 may also be carried by occlusion balloon catheter 80. At midportion 82 of occlusion balloon catheter 80, occlusion balloon inflation tube 85 and occlusion catheter suction tube 86 may be disposed side-by-side. At proximal end portion 83 of the occlusion balloon catheter 80, occlusion balloon inflation tube 85 and occlusion catheter suction tube 86 may be separated and terminate at an occlusion balloon inflation stopcock valve 87 and the occlusion catheter suction connection piece 88, respectively. At distal end portion 81 of occlusion balloon catheter 80, occlusion balloon inflation tube 85 communicates with occlusion balloon 84 and occlusion catheter suction tube 86 passes through occlusion balloon 84 to terminate at an occlusion catheter suction tip 89 that may be used to drain air or water accumulated within the body cavity distal to inflatable occlusion balloon 84.

Distal end portion 81 of occlusion balloon catheter 80 may be independently positioned distal to distal end portion 16 of overtube 11 within the body cavity. Proximal end portion 83 of occlusion balloon catheter 81 may extend out of catheter passageway entrance port 65 on a catheter passageway port projection 64 of overtube 11.

C—Irrigation Tubes:

As it is depicted in FIG. 25, handle 19 may define irrigation port 111 that is capped with a removable irrigation port cap 112 (FIG. 1). Irrigation port cap 112 may be removed when desired, and an irrigation tube system 110 may be connected through irrigation tube connector 113 to irrigation port 111. A clean water irrigation tube 121 and a wastewater irrigation tube 131 may both terminates at the irrigation tube connector 113 side by side.

Clean water can be infused within the examination compartment 95 through the lumen of overtube 11 using clean water irrigation tube 121. The flow of water within clean water irrigation tube 121 may be controlled using a slit valve 122. Clean water irrigation tube 121 may be connected to a container (not shown) of fresh water during irrigation of examination compartment 95 using a connection piece 123.

Wastewater can be drained from the examination compartment 95 through the lumen of overtube 11 using wastewater irrigation tube 131. The flow of water within wastewater irrigation tube 131 may be controlled using a slit valve 132. Wastewater irrigation tube 131 may be connected to a container (not shown) of wastewater during the irrigation of examination compartment 95 using a connection piece 133.

Alternatively, irrigation system 110 may be connected through irrigation tube connector 113 to proximal opening 17 of overtube 11 when endoscope shaft 91 is not in overtube 11. In this configuration, irrigation port 111 may be capped by irrigation port cap 112.

D—Operation.

Endoscope tip 92 may be inserted into a body cavity such as gastrointestinal tract to reach to the desired location within the body cavity. At this time, endoscope accessory sheet 101 is wrapped around endoscope shaft 91 and opposed longitudinal edge portions 107 and 108 coact to form flexible overtube 11 enveloping shaft of endoscope 91 over the portion of shaft 91 that is still outside of the subject's body cavity.

Handle 19 of the overtube 11 may be grasped by endoscopist the distal end portion 16 of overtube 11 may be pushed into the body cavity using endoscope shaft 91 as a guide. Overtube distal end portion 16 may be advanced so that distal end portion 16 of overtube 11 reached to endoscope tip 92 within the body cavity so overtube 11 can be viewed through endoscope and then, it is pulled back just a few centimeters, to ensure that the distal end portion 16 of overtube 11 is situated just proximal to endoscope tip 92 within the body cavity.

At this point, inflatable positioning ring 22 at distal end portion 16 of overtube 11 is inflated to secure the position of overtube 11 within the body cavity.

At this point, endoscope shaft 91 may be removed or replaced with another endoscope, if desired, while overtube 11 is still within the body cavity.

At this point, inflatable sealing band 32 of overtube 11 may be inflated to secure the position of endoscope shaft 91 within overtube 11.

Distal end portion 81 of occlusion balloon catheter 80 may be inserted into catheter passageway entrance port 65 on catheter passageway port projection 64 and passed through catheter passageway 63 and exit from catheter passageway exit port 61 at distal end portion 16 of overtube 11 inside the body cavity. Then, inflatable occlusion balloon 84 at distal end portion 81 of occlusion balloon catheter 80 may be independently positioned distal to the distal end portion 16 of overtube 11 within the body cavity.

Then, inflatable occlusion balloon 84 may be inflated to secure the position of distal end portion 81 of occlusion balloon catheter 80.

Figure 27:
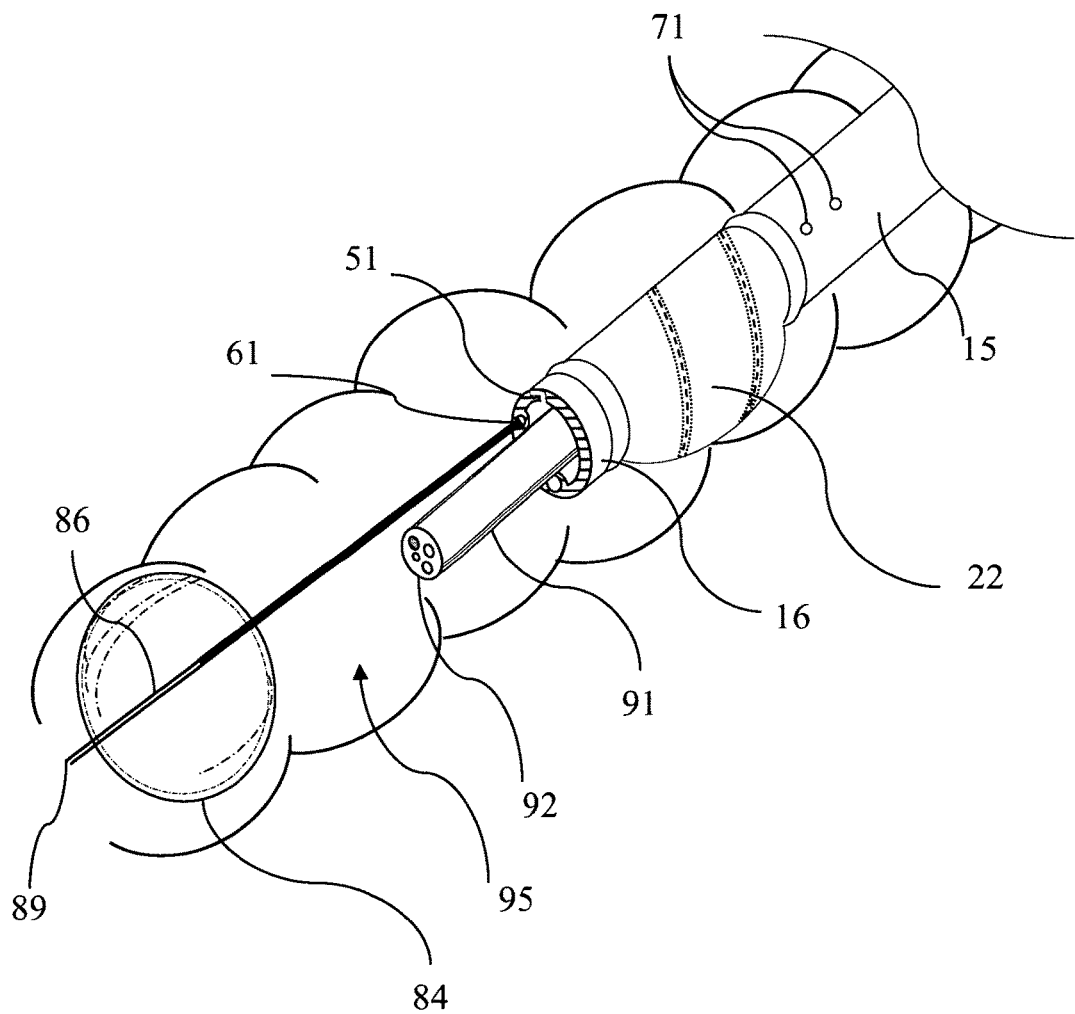
FIG. 27 is a schematic illustration of the endoscope accessory creating an examination compartment within the lower gastrointestinal tract.

As it is depicted in FIG. 27, an examination compartment 95 may be formed around tip 92 of endoscope shaft 91 within the gastrointestinal tract. Examination compartment 95 is formed when inflatable positioning ring 22, inflatable sealing band 32 (FIG. 14) and occlusion balloon 84 are all inflated. Examination compartment 95 may be filled with air or water depending on the procedure application using fluid catheter conduit 44 (FIG. 2), which terminates in fluid conduit port 41 (FIG. 11) at distal end portion 16 of overtube 11.

In an alternative use, examination compartment 95 may also be lavaged with water using irrigation tube system 110 after placement of overtube 11 and inflation of positioning ring 22 and occlusion balloon 84, an irrigation tube system 110 may be connected through irrigation tube connector 113 to irrigation port 111. Water or other fluid may be purged into and drained from examination compartment 95 using irrigation port 111 and irrigation tube system 110 while endoscope shaft 91 is still within overtube 11. Alternatively, examination compartment 95 may be lavaged without need to use irrigation port 111. To do this task, the endoscope could be withdrawn from the body cavity and overtube 11. Irrigation tube system 110 may be connected through irrigation tube connector 113 directly to proximal opening 17 of overtube 11. Water or other fluid may then be purged into and drained from examination compartment 95 using overtube 11 and irrigation tube system 110 while endoscope shaft 91 is not in overtube 11.

The secretions or air at the area proximal to inflated positioning ring 22 may be aspirated using suction conduit port 71 at midportion 15 of overtube 11.

The secretions or air at the area distal to inflated occlusion balloon 84 may be aspirated using occlusion catheter suction tip 89, downstream of occlusion balloon 84.

After completion of the examination, the air or water within examination compartment 95 is drained via fluid conduit port 41. Then, inflated positioning ring 22, inflated sealing band 32 (FIG. 14) and inflated occlusion balloon 84 are all deflated, and overtube 11, occlusion balloon catheter 80 as well as endoscope shaft 91 may be removed independently of each other from the body cavity.

The forgoing description and the drawing are illustrative of the invention and are not to be taken as limiting. Still other variants and rearrangements of structural parts are possible without departing from the spirit and scope of this invention and will readily present themselves to those skilled in the art.

As will also be understood by those skilled in the arts, the order of the steps of the method described above is not critical. The spirit of the invention and the method for employing it are found in the individual features of the invention and their use, not the order in which they are used or presented herein; in fact, the user may elect to eliminate certain steps.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

The scope of the present invention, therefore, is not intended to be limited to the exemplary aspects shown and described herein. Rather, the scope and spirit of present invention is embodied by the appended claims.

I claim:

1. A method for performing an endoscopic procedure comprising the steps of:
    introducing an endoscope into a body cavity, the endoscope further including at least a shaft having a proximal end and a distal end and a tip at its distal end;
    placing a flexible longitudinal sheet that reversibly envelope the endoscope shaft by forming a flexible overtube around the endoscope shaft while the endoscope is still in-part within the body cavity, the flexible longitudinal sheet having first and second faces, a proximal end portion, a midportion, a distal end portion, and opposed longitudinal edge portions coacting to form a flexible overtube when the longitudinal edge portions overlap, the flexible overtube defining an external surface and an internal surface and a central through passageway for receiving therewithin the endoscope shaft, an inflatable pocket on the second face of the sheet, extending across the entire width of the sheet at the distal end portion of the sheet;
    forming an inflatable positioning ring on the external surface of the flexible overtube when the opposed longitudinal edge portions are joined to form the flexible overtube, and an inflatable band at the proximal end of the sheet for forming a sealing band on the internal surface of the flexible overtube when the opposed longitudinal edge portions are joined to form the flexible overtube, wherein the positioning ring is asymmetrical to allow the flexible overtube to be positioned off center to the body cavity and is connected to the external surface at the opposed longitudinal edge portions of the flexible overtube, wherein the longitudinal edge portions have half-thickness edges lengthwise and the half-thickness edges create the longitudinal seam when the longitudinal edge portions overlap, and wherein the inflatable band is eccentric relative to the flexible overtube and is connected to the internal surface at the opposed longitudinal edge portions of the flexible overtube;
    introducing the flexible overtube within the body cavity using the endoscope shaft as the guide until the distal end of the overtube approach to but not pass beyond the endoscope tip;
    inflating the positioning ring to create a seal between the outer surface of the overtube and a body cavity surface such that the inflated ring is proximal to the tip of the endoscope;
    inflating the sealing band to create a seal between the internal surface of the overtube and the endoscope shaft; and
    draining air and fluid from the body cavity accumulated proximal to the positioning ring using a suction conduit carried by the overtube to the midportion and that terminates at a suction conduit port that is proximal to the positioning ring, wherein the draining occurs after the opposed longitudinal edge portions are joined.

2. The method of claim 1, including the further steps:
    introducing examination, diagnostic or therapeutic devices through one or more additional catheter passageways; and
    including a reclosable opening in the proximal end portion of the flexible longitudinal sheet which forms an irrigation port.

3. The method of claim 2, including the further step of suctioning air or fluid through at least one of the one or more additional catheter passageways.

4. The method of claim 2, including the further steps of:
    introducing an independently positionable occlusion catheter having a distal end terminating in an occlusion balloon through one of the one or more additional catheter passageways of the overtube;
    positioning the occlusion catheter distal end distal to the endoscope tip;
    inflating the occlusion balloon to create a seal between the occlusion balloon and the body cavity surface;
    creating an examination compartment that extends from the positioning ring to the occlusion balloon; and,
    introducing fluid or air into the examination compartment through one of the one or more additional catheter passageways in the overtube, the one or more additional catheter passageways extending from the proximal end to the distal end of the overtube.

5. The method of claim 4, including the further step of deflating the occlusion balloon to reposition it to a different point in the body cavity and then reinflating it.

6. The method of claim 4, wherein the occlusion catheter is a double lumen member having a first lumen that communicates with the occlusion balloon for inflating and deflating the occlusion balloon and a second lumen that terminates distal to the examination compartment for aspirating fluid or air distal to the occlusion balloon, including the additional step of aspirating fluid or air distal from the distal the examination compartment.

7. The method of claim 4, including the further steps of:
    deflating the sealing band to release the endoscope within the overtube;
    removing the endoscope from the body cavity and overtube completely; and
    reintroducing another endoscope or therapeutic device into the overtube and the examination compartment.

8. The method of claim 4, including the further steps of:
    deflating the sealing band to release the endoscope within the overtube;
    removing the endoscope from the body cavity and overtube completely;
    connecting an irrigation tube connector to the irrigation port; and
    lavaging the examination compartment using water.

9. The method of claim 2, including the further steps of:
    deflating the sealing band to release the endoscope within the overtube;
    removing the endoscope from the body cavity and overtube completely;
    keeping the irrigation port capped; and
    lavaging the examination compartment using water.

10. The method of claim 8, including the further steps of:
    suctioning air or fluid from the examination compartment;
    deflating the occlusion balloon and withdrawing the occlusion catheter at least partially through the catheter passageway;

deflating the positioning ring; and withdrawing the endoscope and overtube from the body cavity independently or together.

\* \* \* \* \*